US009062119B2

(12) United States Patent
Varga et al.

(10) Patent No.: US 9,062,119 B2

(45) Date of Patent: Jun. 23, 2015

(54) MODIFIED PEPTIDE TOXINS

(71) Applicants: Zoltan Varga, Debrecen (HU); Gyorgy Panyi, Debrecen (HU); Gabor Toth, Szeged (HU); Kinga Rakosi, Szeged (HU)

(72) Inventors: Zoltan Varga, Debrecen (HU); Gyorgy Panyi, Debrecen (HU); Gabor Toth, Szeged (HU); Kinga Rakosi, Szeged (HU)

(73) Assignees: University of Debrecen, Debrecen (HU); University of Szeged, Szeged (HU)

( * ) Notice: Subject to any disclaimer, the term of this patent is extended or adjusted under 35 U.S.C. 154(b) by 0 days.

(21) Appl. No.: 14/354,540

(22) PCT Filed: Oct. 29, 2012

(86) PCT No.: PCT/HU2012/000117

§ 371 (c)(1),
(2) Date: Apr. 25, 2014

(87) PCT Pub. No.: WO2013/061106

PCT Pub. Date: May 2, 2013

(65) Prior Publication Data

US 2015/0087603 A1 Mar. 26, 2015

(30) Foreign Application Priority Data

Oct. 28, 2011 (HU) ..................................... 1100604

(51) Int. Cl.

| | |
|---|---|
| ***A61K 38/00*** | (2006.01) |
| ***A61K 38/28*** | (2006.01) |
| ***A61P 3/10*** | (2006.01) |
| ***A61P 7/12*** | (2006.01) |
| ***A61P 19/02*** | (2006.01) |
| ***A61P 29/00*** | (2006.01) |
| ***C07K 14/47*** | (2006.01) |
| ***A61K 38/16*** | (2006.01) |
| ***C07K 14/435*** | (2006.01) |

(52) U.S. Cl.

CPC ................................ *C07K 14/43522* (2013.01)

(58) Field of Classification Search

None

See application file for complete search history.

(56) References Cited

U.S. PATENT DOCUMENTS

| | | |
|---|---|---|
| 6,861,405 B2 | 3/2005 | Desir et al. |
| 2007/0071764 A1 | 3/2007 | Sullivan et al. |

FOREIGN PATENT DOCUMENTS

| | | |
|---|---|---|
| WO | 2006002850 A2 | 1/2006 |

OTHER PUBLICATIONS

Bagdanyi, M. et al. Anuroctoxin, a new scorpion toxin of the alpha-KTx 6 subfamily, is highly selective for Kv1.3 over IKCa1 ion channels of human T lymphocytes. Mol Pharmacol (2005), vol. 67, pp. 1034-1044.

Batista, CV. et al. Two novel toxins from the Amazonian scorpion *Tityus cambridgei* that block Kv1.3 and Shaker B K(+)-channels with distinctly different affinities. Biochim Biophys Acta (2002), vol. 1601, pp. 123-131.

Beeton, C. et al. Selective blockade of T lymphocyte K+ channels ameliorates experimental autoimmune encephalomyelitis, a model for multiple sclerosis. Proc Natl Acad Sci USA (2001), vol. 98, pp. 13942-13947.

Beeton, C. et al. Kv1.3 channels are a therapeutic target for T cell-mediated autoimmune diseases. Proc Natl Acad Sci USA (2006), vol. 103, pp. 17414-17419.

Corzo, G. et al. A selective blocker of Kv1.2 and Kv1.3 potassium channels from the venom of the scorpion *Centruroides suffusus suffusus*. Biochem Pharmacol (2008), vol. 76, pp. 1142-1154.

Dauplais, M. et al. On the convergent evolution of animal toxins. Conservation of a diad of functional residues in potassium channel-blocking toxins with unrelated structures. J Biol Chem (1997), vol. 272, pp. 4302-4309.

Goldstein, SA. et al. Mechanism of charybdotoxin block of a voltage-gated K+ channel. Biophys J (1993), vol. 65, pp. 1613-1619.

Han, S. et al. Structural Basis of a Potent Peptide Inhibitor Designed for Kv1.3 Channel, a Therapeutic Target of Autoimmune Disease. J Biol Chem (2008), vol. 283(27), pp. 19058-19065.

Jouirou, B. et al. Cobatoxin 1 from *Centruroides noxius* scorpion venom: chemical synthesis, three-dimensional structure in solution, pharmacology and docking on K+ channels. Biochem J (2004), vol. 377, pp. 37-49.

Leonard, RJ. et al. Selective blockers of voltage-gated K+ channels depolarize human T lymphocytes: mechanism of the antiproliferative effect of charybdotoxin. Proc Natl Acad Sci USA (1992), vol. 89, pp. 10094-10098.

M'Barek, S. et al. Synthesis and characterization of Pi4, a scorpion toxin from *Pandinus imperator* that acts on K+ channels. Eur J Biochem (2003), vol. 270, pp. 3583-3592.

Mouhat, S. et al. The 'functional' dyad of scorpion toxin Pi1 is not itself a prerequisite for toxin binding to the voltage-gated Kv1.2 potassium channels. Biochem J (2004), vol. 377, pp. 25-36.

Panyi, G. et al. K+ channel blocker s: novel tools to inhibit T cell activation leading to specific immunosuppression. Curr Pharm Des (2006), vol. 12, pp. 2199-2220.

Panyi, G. et al. Ion channels and lymphocyte activation. Immunol Lett (2004), vol. 92, pp. 55-66.

Papp, F. et al. Tst26, a novel peptide blocker of Kv1.2 and Kv1.3 channels from the venom of *Tityus stigmurus*. Toxicon (2009), vol. 54, pp. 379-389.

Pennington, MW. et al. Engineering a stable and selective peptide blocker of the Kv1.3 channel in T lymphocytes. Mol Pharmacol (2009), vol. 75, pp. 762-773.

Peter, M. et al. Blockage of human T lymphocyte Kv1.3 channels by Pi1, a novel class of scorpion toxin. Biochem Biophys Res Commun (2000), vol. 278, pp. 34-37.

Peter, M. et al. Effects of toxins Pi2 and Pi3 on human T lymphocyte Kv1.3 channels: the role of Glu7 and Lys24. J Membrane Biol (2001), vol. 179, pp. 13-25.

Pimentel, C. et al. Chemical synthesis and 1H-NMR 3D structure determination of AgTx2-MTX chimera, a new potential blocker for Kv1.2 channel, derived from MTX and AgTx2 scorpion toxins. Protein Sci (2008), vol. 17, pp. 107-118.

(Continued)

*Primary Examiner* — Marcela M Cordero Garcia

*Assistant Examiner* — Sergio Coffa

(74) *Attorney, Agent, or Firm* — Seth D. Levy; Nixon Peabody LLP

(57) ABSTRACT

The invention relates to toxin peptides capable of selectively inhibiting a Kv1.3 potassium channel protein. The toxin peptides of the invention are modified anuroctonus scorpion toxin peptides.

22 Claims, 5 Drawing Sheets

(56) References Cited

OTHER PUBLICATIONS

Srinivasan, KN. et al. kappa-Hefutoxin1, a novel toxin from the scorpion *Heterometrus fulvipes* with unique structure and function: Importance of the functional diad in potassium channel selectivity. J Biol Chem (2002), vol. 277, pp. 30040-30047.

Tucker, K. et al. Kv1.3 gene-targeted deletion alters longevity and reduces adiposity by increasing locomotion and metabolism in melanocortin-4 receptor-null mice. International Journal of Obesity (2008), pp. 1-11.

Varga, Z. et al. Vm24, a natural immunosuppressive peptide, potently and selectively blocks Kv1.3 potassium channels of human T cells. Mol Pharmacol (2012), vol. 82(3), pp. 372-382.

Visan, V. et al. Mapping of maurotoxin binding sites on hKv1.2, hKv1.3, and hIKCa1 channels. Mol Pharmacol (2004), vol. 66, pp. 1103-1112.

Wulff, H. et al. The voltage-gated Kv1.3 K+ channel in effector memory T cells as new target for MS. J Clin Invest (2003), vol. 111, pp. 1703-1713.

Yin, SJ. et al. Different Residues in Channel Turret Determining the Selectivity of ADWX-1 Inhibitor Peptide between Kv1.1 and Kv1.3 Channels. J Prot Res (2008), vol. 7(11), pp. 4890-4897.

NMR structure of synthetic AnTx and its N17A, F32T mutant (side view 1)

NMR structure of synthetic AnTx and its N17A, F32T mutant (side view 2)

MODIFIED PEPTIDE TOXINS

CROSS-REFERENCE TO RELATED APPLICATIONS

This application is a National Phase of International Application No. PCT/HU2012/000117, filed Oct. 29, 2012, which designated the U.S. and that International Application was published under PCT Article 21(2) in English. This application also includes a claim of priority under 35 U.S.C. §119(a) and §365(b) to Hungarian patent application No. P1100604, filed Oct. 28, 2011.

The invention relates to toxin peptides capable of selectively inhibiting a Kv1.3 potassium channel protein. The toxin peptides of the invention are modified anuroctonus scorpion toxin peptides.

Ion Channels as Potential Targets in the Treatment of Autoimmune Diseases

During the course of an autoimmune disease the immune system attacks the organism's own cells and tissues, such as the insulin producing cells in type I diabetes or the insulating cover of neuronal axons in the brain in multiple sclerosis. The general immunosuppression that can be utilized for the treatment of such diseases compromises the organism's ability to protect itself from pathogens, thus, occasionally serious side effects may ensue. A special group of T lymphocytes, the chronically activated effector memory T cells ($T_{EM}$), have been implicated in the development of these diseases (Beeton et al., 2006).

The cell membrane surrounding every cell incorporates gated pores, ion channels, which allow selective passage of ions across the membrane and are thus named $Na^+$, $K^+$ or $Ca^{2+}$ etc. channels. These ion channels are essential for numerous cellular functions, such as transport mechanisms, volume and osmo-regulation, signal transduction, differentiation and proliferation. Considering their critical roles, the ion channels of T lymphocytes, one group of the key players of cellular immunity, serve as targets for modulating immune functions via lymphocyte activity (Leonard et al., 1992). In order to exploit this possibility, we must know the precise role of these channels in T cell function and find molecules that specifically bind to them and modulate their operation.

Significance of $K^+$ Channels During T Cell Activation

A major step of the cellular immune response is the proliferation and differentiation of antigen-specific lymphocytes. An important element of the signaling cascade through the T cell receptor is the rise in intracellular $Ca^{2+}$ concentration. During the $Ca^{2+}$ signal $Ca^{2+}$ is first released from intracellular stores, then activated by the emptying of these stores $Ca^{2+}$ enters the cell through $Ca^{2+}$ release activated $Ca^{2+}$ (CRAC) channels. The driving force required by the adequate influx is provided by the $K^+$ channels of T cells by compensating the depolarizing effect of the $Ca^{2+}$ influx by $K^+$ efflux (Panyi et al., 2004). By now numerous experiments prove that the blockade of the $K^+$ channels playing a critical role in the $Ca^{2+}$ signal required for T cell activation leads to the inhibition of proliferation of T cells in vitro and in vivo. An important finding of recent years is that naïve, central memory and effector memory T cells identified by their expression of the chemokine receptor CCR7 and the phosphatase CD45RA have different $K^+$ channel expression patterns (Wulff et al., 2003). Thus, the activation of T cells may depend primarily on the voltage-gated Kv1.3 or the $Ca^{2+}$-activated $K_{Ca}3.1$ channels depending on their differentiation state. Accordingly, the proliferative response of the various T cell subpopulations can be inhibited by channel blocking compounds specific for Kv1.3 or $K_{Ca}3.1$ channels.

It is especially important that effector memory T cells ($CCR^-7CD45RA^-$), which are major contributors to the pathogenesis of several autoimmune diseases (multiple sclerosis, type I diabetes) express Kv1.3 channels in much higher numbers than naive ($CCR7^+CD45RA^-$) and central memory ($CCR7^+CD45RA^-$) T cells and consequently their proliferation relies acutely on the operation of these channels. Thus, the progression of certain autoimmune diseases may be controlled with Kv1.3 blockers of high affinity and specificity, and these compounds could serve as the basis for the development of drugs for the treatment of autoimmune diseases in the future. Using such a high affinity potassium channel blocking toxin the symptoms of experimental autoimmune encephalomyelitis (EAE), which serves as a model of multiple sclerosis could be ameliorated in experimental animals (Becton et al., 2001b). This is of great importance because today many drugs exist that act by affecting ion channels in various cells (especially muscle cells and neurons), but the manipulation of the cells of the immune system via ion channels is still a practically untouched area holding great potential.

Peptide Toxins from Scorpion Venom as Channel Blocking Agents

Peptide toxins from the venoms of various species including scorpions were identified as high affinity channel blockers early in the ion channel research era. With the use of these toxins a large body of information was gathered about the structure and the structure-function relationship of ion channels. Since then dozens of new toxins were found to block the passage of ions through the targeted channels with varying affinities and selectivities and by this, affect a wide repertoire of cellular functions (Panyi et al., 2006). Most of these peptides are structurally similar, consisting of 35-40 amino acids, two anti-parallel β-sheets, a short α-helix, 3 or 4 disulphide bridges and a conserved lysine whose positively charged side chain protrudes into the selectivity filter of the channel upon binding (Goldstein and Miller, 1993a). In this case the toxin plugs the pore of the channel preventing the passage of $K^+$ ions.

In the last decade significant experience has accumulated in the area of scorpion toxins, especially in the identification of peptides blocking the Kv1.3 channel found in T cells (Peter et al., 2000; Peter et al., 2001; Batista et al., 2002; Corzo et al., 2008; Papp et al., 2009). The present inventors have isolated and characterized several scorpion toxins that block Kv1.3 in the pM-nM concentration range. For a toxin to be available for potential therapeutic application it is essential that it should only block the ion channel involved in the targeted function of the target cell without influencing other channels. This requirement is crucial in avoiding side effects. For example, Kv channel subunits closely related to Kv1.3, such as Kv1.2 or Kv1.6, form channels in the nervous system, whose blockade may have disastrous effects. Thus, for compounds developed for the treatment of T cell mediated autoimmune diseases high selectivity for Kv1.3 is just as an important prerequisite as high affinity for the channel.

Han, S et al. have applied a structural approach [Han S et al, *J Biol Chem* 2008; 283(27):19058-19065.] to improve Kv1.3 selectivity of scorpion toxins. The authors started from the BmKTX scorpion toxin (*Bhutus martensi*) and designed a peptide with three point mutations based on binding studies to the Kv1.3 K channel at the molecular interaction level. Specifically, glycine (G) 11 was substituted with arginine (R), isoleucine (I) 28 with threonine (T) and aspartate (D) 33 with histidine (H) (BmKTX-Arg11Thr28His33 or ADWX-1 in short). While the ADWX-1 peptide was reported to block Kv1.3 with an IC50 value of 1 mM by the authors, later Cahalan M D and Chandy K G found this peptide to have an IC50 value of 1.2 nM i.e. a 1000 fold lower potency [Cahalan M D and Chandy K G, *Immunol Rev.* 2009 231(1): 59-87.].

Soon after the work of Han, S et al. (see above) was published, Yin S J et al. have shown, using combined approaches, that the Kv1 turret is the critical determinant for ADWX-1 peptide inhibitor selectivity of Kv1.3 over Kv1.1 and mutation of Kv1.1 turret residues to match the sequence of Kv1.3 lead to increased inhibition of Kv1.1 activity [Yin S J et al. *J Prot Res* 2008; 7(10:4890-4897.].

Mouhat Stephanie et al. also applied an approach including site specific mutation of scorpion toxin peptides in WO2006002850A2. The authors started from *Orthochirus scrobiculosus* scorpion toxin and suggest that in position 16 a lysine (K) and in position 20 an aspartate (D) should be present, whereas the conserved histidine (H) at position 34 should be replaced with alanine (A) so as to increase specificity.

Sullivan John K. in US20070071764A1 disclose a number of toxin peptide analog of ShK, OSK1, ChTx or Maurotoxing scorpion toxin peptides having greater Kv1.3 or IKCa1 antagonist activity and/or target selectivity compared to corresponding wild type peptides having a native sequence. While the authors mention Fc-L-Anuroctoxin it appears that no mutant is suggested having an altered selectivity.

In these channel-toxin interactions the amino acid sequences of the partners determine the quality of the interaction. The two partners of the interacting pair should have complementary surfaces that match well to form several strongly binding contact points based on electrostatic and hydrophobic interactions. Minor alterations in the sequence of either partner may cause major spatial constraints on toxin docking or change the nature of the interactions, which consequently can drastically influence the affinity of binding.

Anuroctoxin

Anuroctoxin is a peptide toxin belonging to the α-KTx family of scorpion toxins isolated from the venom of the Mexican scorpion *Anuroctonus phaiodactilus*. It consists of 35 amino acids cross-linked by four disulphide bridges with a molecular weight of 4082.8. Anuroctoxin is a potent blocker of the voltage-gated potassium channel Kv1.3 ($K_d$=0.73 nM). However it blocks the voltage-gated potassium channel Kv1.2 with a lower, but still remarkable affinity ($K_d$=6.14 nM) (Bagdany et al., 2005).

As compared to the peptide disclosed by Han, S et al., above, in positions of anuroctoxin corresponding to the positions 11, 28 and 33 of BmKTX glutamine (Q), methionine (M) and lysine (K) can be found, respectively, whereas if compared to the modified *Orthochirus scrobiculosus* scorpion toxin, in corresponding positions of the wild type anuroctoxin asparagine (N), lysine (K) and lysine (K) can be found, respectively. It appears that no mutant anuroctonus scorpion toxin having an improved Kv1.3 has been disclosed in the prior art.

The study of the present inventors aimed at the improvement of the channel-toxin interaction by increasing the selectivity and affinity of anuroctoxin for Kv1.3 based on directed mutations in its sequence.

BRIEF DESCRIPTION OF THE INVENTION

The invention relates to a toxin peptide capable of selectively inhibiting a Kv1.3 potassium channel protein, said peptide having or consisting essentially of 32 to 36 amino acid residues, more preferably 33, 34 or 35 amino acid residues)

said peptide having four disulphide bridges, wherein said peptide comprises, has, includes or consists of the following amino acid sequence (SEQ ID NO: 7):

| | | | | | | | | | |
|---|---|---|---|---|---|---|---|---|---|
| 1 | 2 | 3 | 4 | 5 | 6 | 7 | 8 | 9 | 10 |
| Z | $X_1$ | $X_2$ | $C_1$ | $X_3$ | $X_4$ | $X_5$ | $X_6$ | $X_7$ | $C_2$ |
| 11 | 12 | 13 | 14 | 15 | 16 | 17 | 18 | 19 | 20 |
| $X_8$ | $X_9$ | $X_{10}$ | $C_3$ | $X_{11}$ | $X_{12}$ | $\mathbf{X_{13}}$ | $K_1$ | $C_4$ | $T_1$ |
| 21 | 22 | 23 | 24 | 25 | 26 | 27 | 28 | 29 | 30 |
| $X_{14}$ | $\mathbf{G_1}$ | $\mathbf{K_2}$ | $C_5$ | $X_{15}$ | $\mathbf{N_1}$ | $R_1$ | $\mathbf{K_3}$ | $C_6$ | $X_{16}$ |
| 31 | 32 | 33 | 34 | 35 | | | | | |
| $C_7$ | $\mathbf{T_1}$ | $N_2$ | $C_8$ | $X_{17}$ | | | | | |

wherein

| Pos. | |
|---|---|
| 1 | Z is pyroglutamate, glutamate (E), aspartate (D), asparagine (N) or glutamine (Q), |
| 2 | $X_1$ is lysine (K) or arginine (R) or nothing, |
| 3 | $X_2$ is glutamate (E) or aspartate (D) or nothing |
| 4 | $C_1$ is cysteine |
| 5 | $X_3$ is threonine (T) or serine (S) |
| 6 | $X_4$ is glycine (G) or alanine (A) |
| 7 | $X_5$ is proline (P) or serine (S) |
| 8 | $X_6$ is glutamine (Q), asparagine (N), glutamate (E), aspartate (D) or lysine (K) |
| 9 | $X_7$ histidine (H), phenylalanine (F), aspartate (D) or glutamine (Q) |
| 10 | $C_2$ is cysteine |
| 11 | $X_8$ is threonine (T), serine (S), alanine (A), leucine (L) or isoleucine (I), |
| 12 | $X_9$ is asparagine (N), glutamate (E), glutamine (Q) or lysine (K), |
| 13 | $X_{10}$ is phenylalanine (F), proline (P) or histidine (H), |
| 14 | $C_3$ is cysteine |
| 15 | $X_{11}$ is lysine (K) or arginine (R), |
| 16 | $X_{12}$ is lysine (K) or aspartate (D) wherein preferably if $X_{12}$ is lysine (K) then $X_{13}$ is alanine (A) or asparagine (N), whereas if $X_{12}$ is aspartate (D) then $X_{13}$ is asparagine (N) |
| 17 | $X_{13}$ is A is alanine (A) or asparagine (N) wherein preferably if $X_{12}$ is lysine (K) then $X_{13}$ is alanine (A) or asparagine (N), whereas if $X_{12}$ is aspartate (D) then $X_{13}$ is asparagine (N) |
| 18 | $K_1$ is lysine (K) |
| 19 | $C_4$ is cysteine |
| 20 | $T_1$ is threonine (T) |
| 21 | $X_{14}$ is histidine (H) or tyrosine (Y) |
| 22 | $G_1$ is glycine |
| 23 | $K_2$ is lysine (K) |
| 24 | $C_5$ is cysteine, |
| 25 | $X_{15}$ is methionine (M), threonine (T) or norleucine (Nor), |
| 26 | $N_1$ is asparagine, |
| 27 | $R_1$ is arginine (R) |
| 28 | $K_3$ is lysine |
| 29 | $C_6$ is cysteine, |
| 30 | $X_{16}$ is lysine (K) or glycine (G) |
| 31 | $C_7$ is cysteine, |
| 32 | $T_1$ is threonine. |
| 33 | $N_2$ is asparagine (N) |
| 34 | $C_8$ is cysteine, |
| 35 | $X_{17}$ is lysine (K) or arginine (R) |

In a preferred embodiment, the toxin peptide is selected from the following group of peptides:

```
                                    (SEQ ID NO: 2)
<EKECTGPQHC TNFCRKNKCT HGKCMNRKCK CTNCK,

                                    (SEQ ID NO: 3)
<EKECTGPQHC TNFCRDNKCT HGKCMNRKCK CTNCK,

                                    (SEQ ID NO: 4)
<EKECTGPQHC TNFCRKAKCT HGKCMNRKCK CTNCK,
```

-continued (SEQ ID NO: 5)

<EKECTGPQHC TNFCRDAKCT HGKCMNRKCK CTNCK, or a mutant or variant thereof comprising at most 12, 11, 10, 9, 8, 7, 6, 5, 4, 3, 2 or 1 amino acid substitutions as defined in claim 1 in the region spanning amino acids 1 to 15 of the toxin peptide sequence, wherein at least the cysteine residues are maintained and/or comprising a substitution at position 35 as defined above. In a further embodiment one or both of the amino acids in positions 16 and 17 are substituted as defined above. In a further embodiment at most 2 or 1 amino acids are deleted, preferably as defined above, i.e. wherein the meaning of $X_1$ and/or $X_2$ is nothing.

In the brodest sense, in the formula or sequence defined above, the amino acid residues in the positions wherein more than one variant is possible, can be varied independently from amino acids in other positions. In a more particular embodiment the variants in certain or multiple positions or in each position may depend from the specific variant in an other position. It is, however, within the skills of a person skilled in the art to screen for the functional features of the peptide as disclosed herein, for example to assay the dissociation constant of the peptides for Kv1.2 potassium channel protein and identify a peptide having a sufficiently high dissociation constant to work as a toxin. Moreover, it is within the skills of a person skilled in the art to assess selectivity of the toxin peptide against Kv1.2 as disclosed herein and identify a peptide having a sufficiently high selectivity to work as a selective toxin.

Preferably in the toxin peptide the dissociation constant ($K_{d,Kv1.2}$) of the peptide for Kv1.2 potassium channel protein is higher than 1000 nM, preferably higher than 1200 nM, more preferably higher than 1500 nM, the dissociation constant ($K_{d,Kv1.3}$) of the peptide for Kv1.3 potassium channel protein is lower than 10 nM, preferably lower than 7 nM, more preferably lower than 3 nM or 1 nM.

Preferably the selectivity of the toxin peptide for Kv1.3 against Kv1.2 (i.e. the ratio of $K_{d,Kv1.2}$ and $K_{d,Kv1.3}$) is higher than 100, preferably higher than 400, more preferably higher than 700, more preferably higher than 1000, more preferably higher than 2000, more preferably higher than 2100, 2200 or 2300.

The invention also relates to the toxin peptide according to the invention for use in the treatment or prevention of a T cell mediated autoimmune disorder, preferably in the treatment or prevention of multiple sclerosis, systemic sclerosis, type-1 diabetes, rheumatoid arthritis, psoriatic arthritis, or psoriasis.

The invention also relates to the toxin peptide according to the invention for use in the treatment or prevention of metabolic syndrome, obesity and type II diabetes mellitus.

The invention also relates to a method for treating or preventing a disease as defined herein said method comprising the step of administering a toxin peptide according to the invention to a patient in need thereof in an amount effective to alleviate at least one symptom of said disease. The invention also relates to a method for inhibiting Kv1.3 with a peptide according to the invention either in vivo, in vitro or ex vivo. The invention also relates to a use of the toxin peptide according to the invention for inhibiting a Kv1.3 potassium channel protein, preferably ex vivo or in vitro and/or to a use of the toxin peptide according to the invention as a competitive inhibitor of a natural or artificial Kv1.3 agonist.

Preferably, the Kv1.3 potassium channel protein is of vertebrate, mammalian or human origin.

Typically, in the present invention substitutions at positions 1-15 are based on literature wherein Kv1.3 selective peptides contain the indicated variations of amino acids in these positions. Positions 1-15 are in the region of the toxin which faces away from the interaction surface with the ion channel, and thus, substitutions, preferably conservative substitutions are preferably better tolerated in these positions without compromising the pharmacological properties. As disclosed herein substitutions at positions 16, 17 and 32 are all based on the experimental data of the inventors. The amino acid in position 35 is away from the interaction surface therefore conservative mutation is preferably tolerated. It is reasonable to assume that in position 25 peptides containing norleucin show higher stability without compromising the pharmacological properties (Pennington M W, Beeton C, Galea C A, Smith B J, Chi V, Monaghan K P, Garcia A, Rangaraju S, Giuffrida A, Plank D, Crossley G, Nugent D, Khaytin I, Lefievre Y, Peshenko I, Dixon C, Chauhan S, Orzel A, Inoue T, Hu X, Moore R V, Norton R S, Chandy K G., Mol Pharmacol 75:762-773, 2009)

Typically, the following cysteine residues form a disulphide bridge (a cystine pair):

C1 and C5,
C2 and C6,
C3 and C7 and
C4 and C8.

DEFINITIONS

A "peptide" is understood herein as a molecule comprising or composed of amino acid residues linked by peptide bonds and having a well-defined amino acid sequence. Typically a peptide consists of at most 100, preferably at most 60, 50 or 40 amino acid residues. The position of an amino acid is the number of said amino acid calculated from the N-terminal of the peptide or, if amino acid sequences of two or more peptides are aligned, it may be construed as the number of the corresponding amino acid in an aligned sequence, e.g. reference sequence calculated from the N-terminal of said sequence.

"Substitution" of an amino acid residue in a peptide is understood herein as the replacement of said amino acid residue by a chemically different amino acid residue. This can be carried out typically by peptide synthesis methods or, if said peptide is prepared by recombinant nucleic acid technology, by protein engineering methods.

"Variant" of a peptide is typically a similar but different, eg. a mutant version thereof. Variant of an amino acid in a given position is an amino acid by which it can be substituted in accordance with the present invention.

The term "comprising" given elements or species or moieties is understood herein as containing said elements (e.g. features or species or moieties) and optionally further elements as well, i.e. comprising does not exclude the presence of further elements. The terms comprising and including are interchangeable herein. The expression "consisting essentially of" is understood herein as comprising only those elements which are given as essential elements and even if further elements are present they do not contribute substantially to the effect of the invention and are not harmful either. The term comprising can be limited to consisting essentially of or consisting of without addition of new matter.

The indefinite articles "a" and "an" may be construed as referring to either singular or plural, e.g. multiple elements may be present.

Dose-response relationships of the synthetic wild-type toxin and the single and double mutants on Kv1.3 channels The blocking efficiency of the toxins was tested on activated lymphocytes. The remaining current fraction (RCF) was calculated as $I/I_0$, where I and $I_0$ represent the whole-cell current amplitude in the presence and absence of the toxin at the indicated concentrations, respectively. Data points are plotted with error bars representing SEM and were fitted with a Hill-equation to obtain the $K_d$ of the binding.

FIG. 2

Blocking efficiency of the synthetic wild-type toxin and the single and double mutants on voltage-gated channels Kv1.1, Kv1.2 and Kv1.3 and the $Ca^{2+}$-activated $K^+$ channel $K_{Ca}3.1$. All the mutants were selective for Kv1.3, since they did not block any of the other tested channels.

FIG. 3

Figure 1:
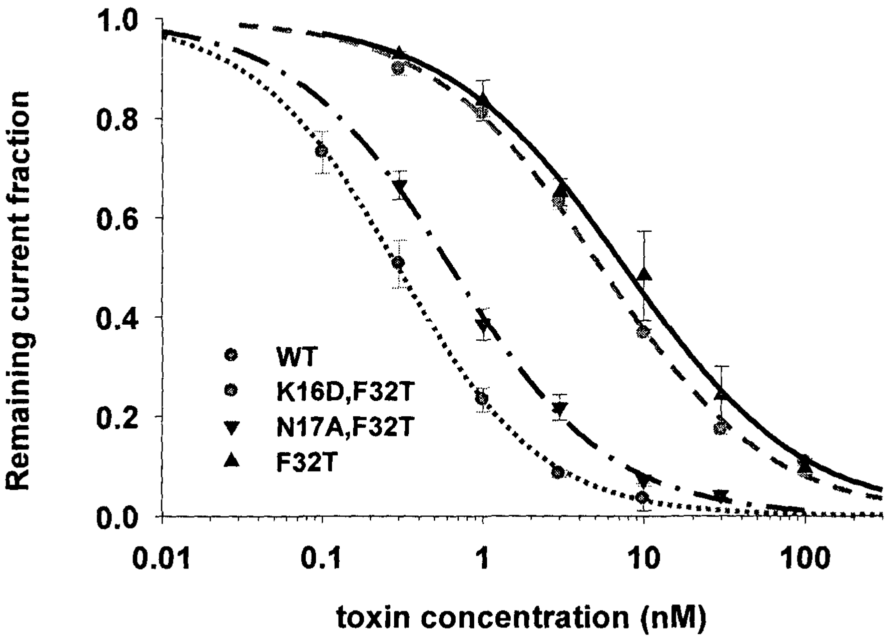
FIG. 1
Figure 2:
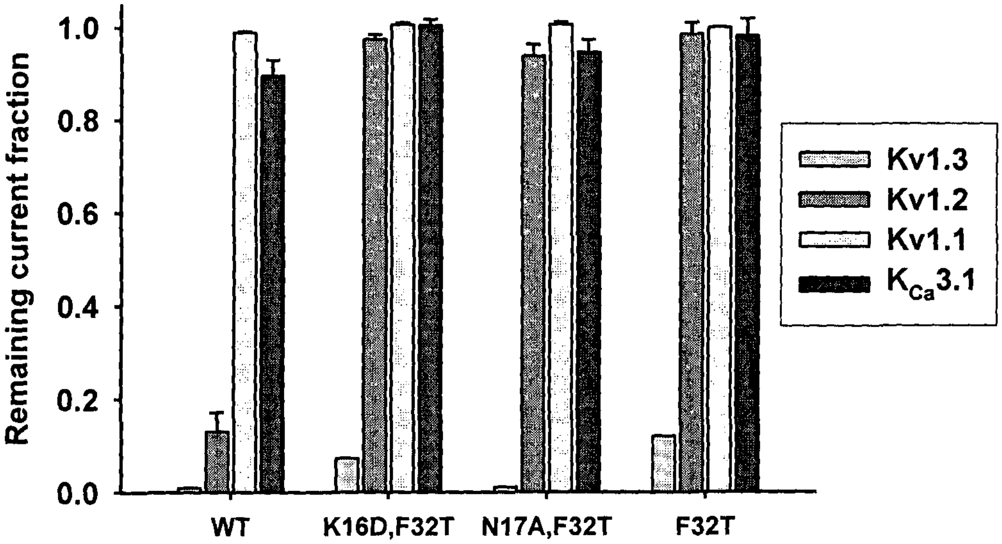
Figure 3:
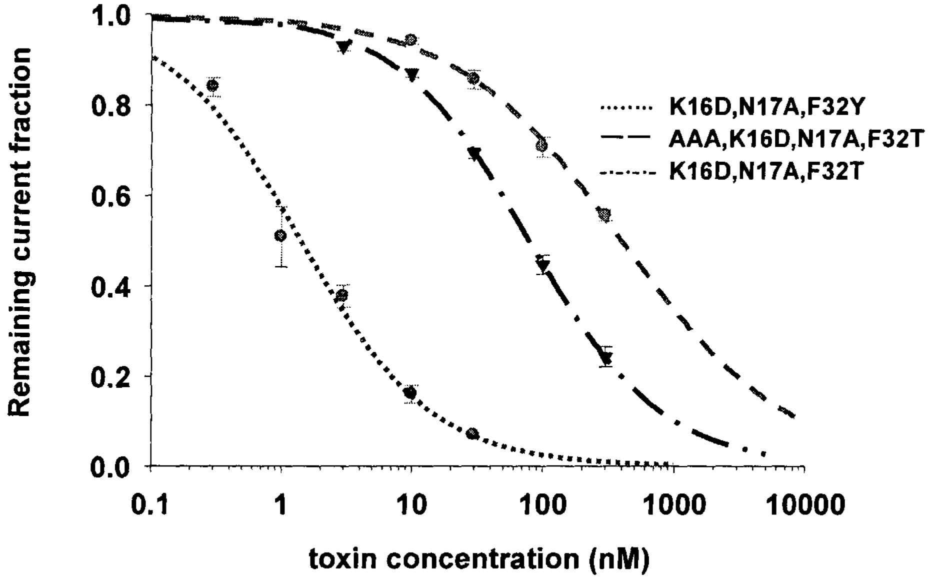
Figure 4:
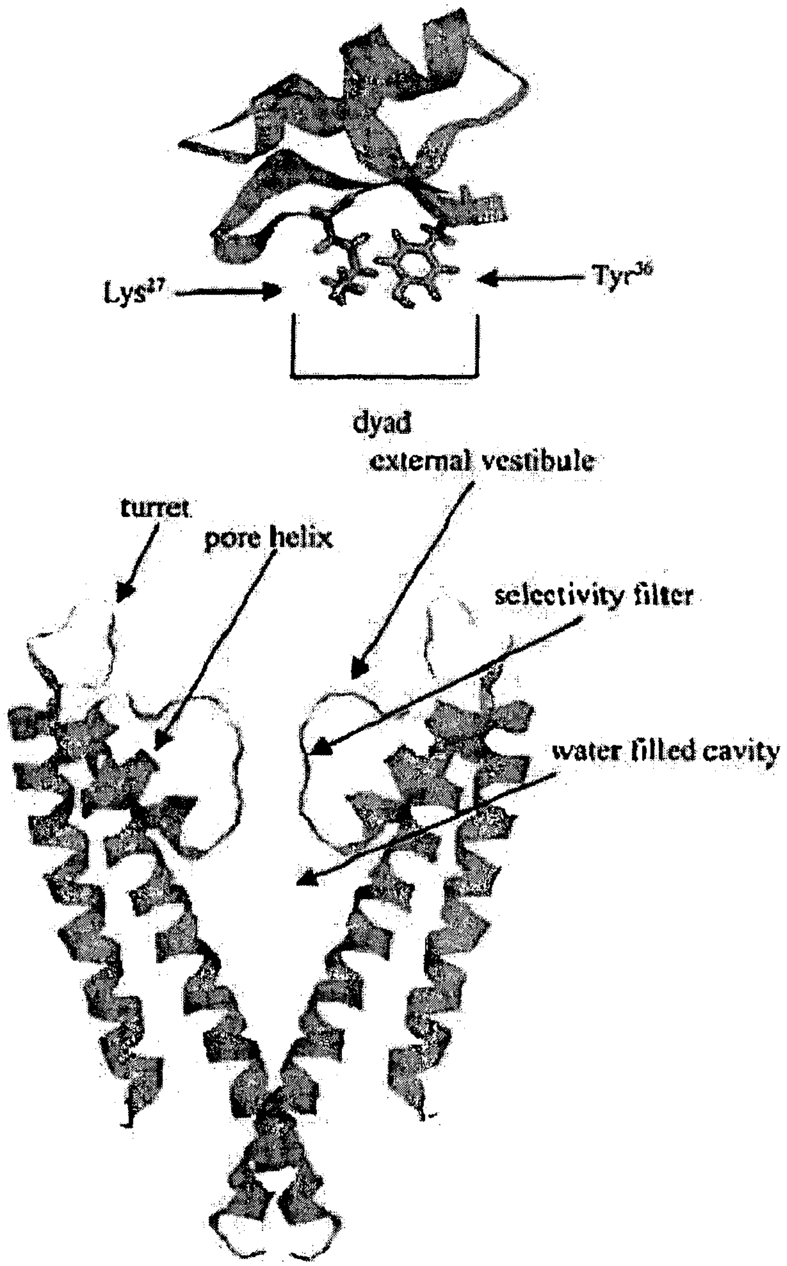
Figure 5:
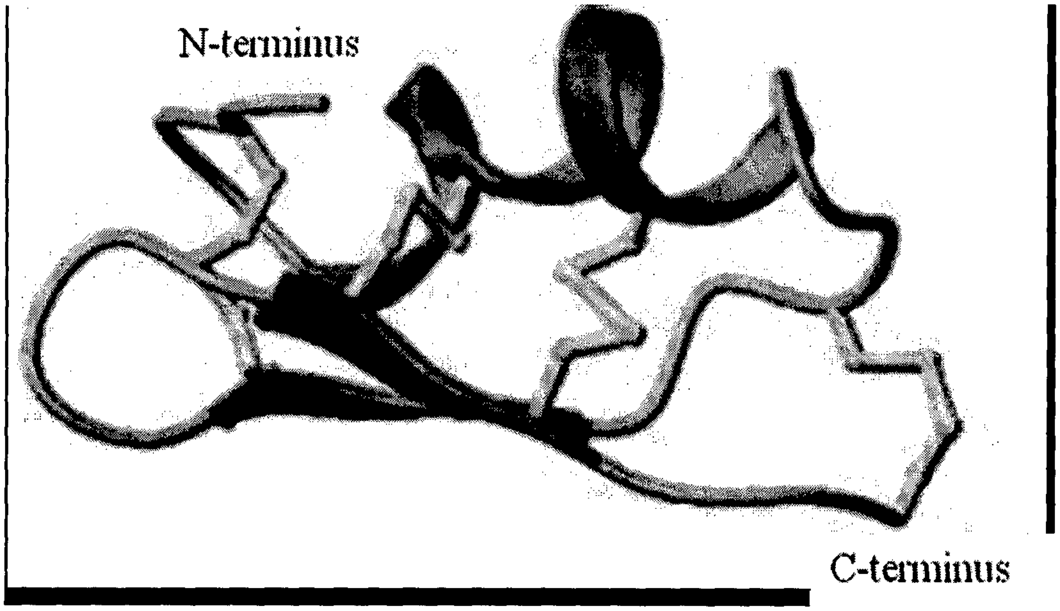
Figure 6:
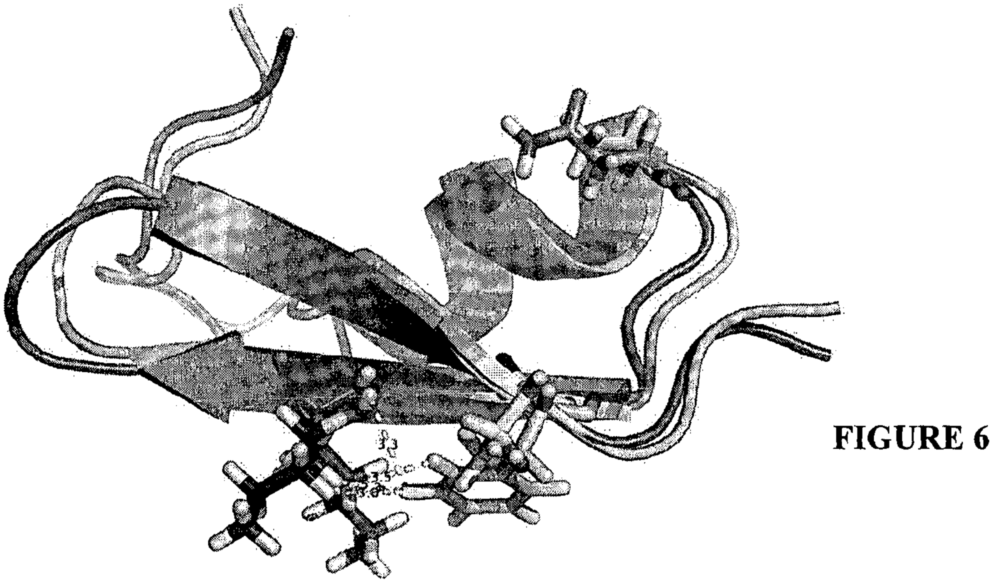
Figure 7:
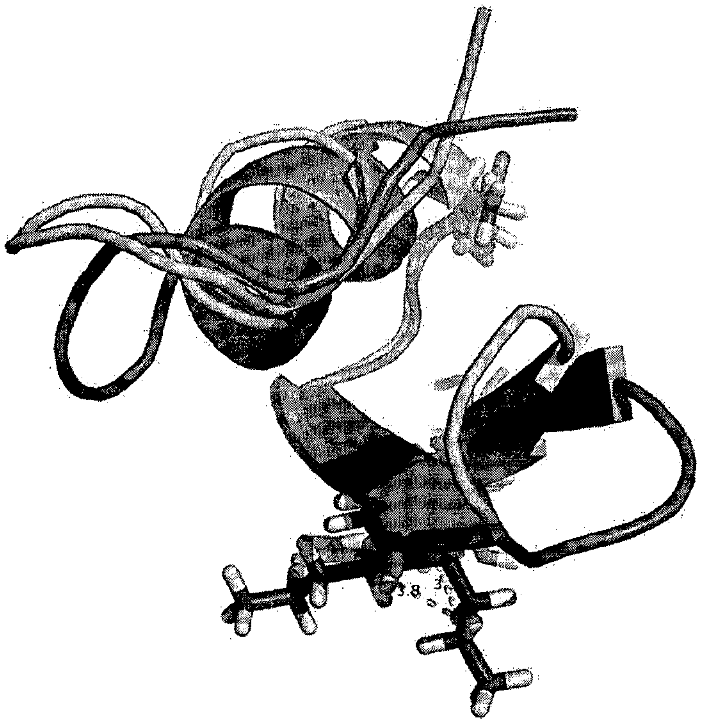

Dose-response relationships of two triple mutant toxins and the triple mutant with the modified N-terminus on Kv1.3 channels. Conditions were the same as for FIG. 1. All three toxins had reduced affinity for Kv1.3 compared to the synthetic wild-type toxin.

FIG. 4

A schematic representation of a toxin structure having a Lys27-Tyr36 dyad shown with the part of the channel comprising the turret and the pore helix and forming the external vestibule, the selectivity filter and a water filled cavity behind them.

FIG. 5

A schematic representation of a homology model of the AnTx.

FIG. 6

NMR structure of synthetic AnTx and its N17A, F32T mutant overlapped—side view 1

FIG. 7

NMR structure of synthetic AnTx and its N17A, F32T mutant overlapped—side view 2

DETAILED DESCRIPTION OF THE INVENTION

The inventors have unexpectedly recognized that selectivity of anuroctonus scorpion toxin towards Kv1.3 receptor can be significantly improved if certain or at least one or more particular amino acids are replaced in the wild type sequence. Thus, novel Kv1.3 blockers have been obtained.

Thereby, progression of certain autoimmune diseases may be controlled with these Kv1.3 blockers of high affinity and specificity, and these compounds could serve as the basis for the development of drugs for the treatment of autoimmune diseases in the future. Using such a high affinity potassium channel blocking toxin the symptoms of experimental autoimmune encephalomyelitis (EAE), which serves as a model of multiple sclerosis could be ameliorated in experimental animals (Beeton et al., 2001a). This is of great importance because today many drugs exist that act by affecting ion channels in various cells (especially muscle cells and neurons), but the manipulation of the cells of the immune system via ion channels is still a practically untouched area holding great potential.

Desir G. et al. have found that inhibiting Kv1.3 activity mediates decreased food intake, weight loss, decreased body fat, increase glucose uptake, and increased insulin sensitivity (U.S. Pat. No. 6,861,405). Moreover, gene-targeted deletion could reduce adiposity and total body weight in a genetic model of obesity by increasing both locomotor activity and mass-specific metabolism; moreover significantly extended lifespan and increased reproductive success have been observed [Tucker K et al., *International Journal of Obesity* (2008), 1-11.].

In type I diabetes, which is an autoimmune disease, Kv1.3 expressing T-lymphocytes attack pancreatic islets, Loss of insulin producing beta cells is a major phenomenon of the disease (Beeton C, Wulff H, Standifer N E, Azam P, Mullen K M, Pennington M W, Kolski-Andreaco A, Wei E, Grino A, Counts D R, Wang P H, LeeHealey C J, S Andrews B, Sankaranarayanan A, Homerick D, Roeck W W, Tehranzadeh J, Stanhope K L, Zimin P, Havel P J, Griffey S, Knaus H G, Nepom G T, Gutman G A, Calabresi P A, Chandy K G.: Kv1.3 channels are a therapeutic target for T cell-mediated autoimmune diseases. Proc Natl Acad Sci USA. 2006, 103:17414-1719.) Blockade of Kv1.3 decreases the level of inflammatory cytokines and facilitates the translocation of GLUT4 to the plasma membrane, the latter effect increasing insulin sensitivity [Sullivan J K et al., US 2007/0071764].

This way, the Kv1.3 blockers of the invention may be useful in the treatment of metabolic syndrome, type II diabetes related therewith, as well as type I diabetes.

Design of Mutations to Improve AnTx Selectivity for Kv1.3

Many of the scorpion toxins blocking Kv channels contain a critically positioned pair of residues, which has been referred to as the "functional dyad" or "essential dyad" made up of the conserved lysine (K23 in AnTx) and an aromatic residue approximately 6-7 angstroms away (usually 9 positions downstream of the lysine, F32 in AnTx) (Dauplais et al., 1997b; Srinivasan et al., 2002). The side chain of the critical lysine strongly interacts with the negatively charged selectivity filter of the channel (Goldstein and Miller, 1993b). The "functional dyad" was originally proposed to be necessary for high affinity block of Kv channels in general, but with more information available it seems to be critical for the high affinity block of Kv1.2, but not so much for Kv1.3. The aromatic dyad residue is a tyrosine in most toxins blocking Kv1.2 with high affinity. Both dyad residues proved essential for high affinity binding to Kv1.2 in Pi1 (K24 and Y33) and maurotoxin (MTX, K23 and Y32), two toxins preferring Kv1.2 over Kv1.3 (Mouhat et al., 2004; Visan et al., 2004c). While the necessity of the dyad lysine was shown for other Kv channels as well (Dauplais et al., 1997a), the requirement for the aromatic half of the dyad, especially the tyrosine, is not as straightforward for blocking Kv1.3. Although block of Kv1.3 in the nanomolar range by toxins bearing a tyrosine at the aromatic dyad position is exemplified by charybdotoxin (ChTx), Css20, Tst26, noxiustoxin, hongotoxin-1 and Pi1, the selectivity for Kv1.3 seems to benefit from the replacement of this tyrosine by other residues. Many effective natural scorpion peptide inhibitors of Kv1.3 have a residue at the "aromatic dyad position" different from tyrosine such as phenylalanine (Pi2, Pi3, anuroctoxin), threonine (kaliotoxin, OSK1, BmKTX) or even asparagine (HsTx1), whereas a tyrosine is located at this position in toxins favoring Kv1.2 over Kv1.3 (MTX, Pi1, CoTX1, Pi4). This suggest that the presence of tyrosine at this position is rather disadvantageous if a Kv1.3 selective toxin is to be designed. This difference may stem from the presence of a histidine residue at position 399 in hKv1.3 at the external entryway of the pore, which prevents high affinity binding to a tyrosine. The equivalent V381 residue of hKv1.2 was shown to interact with the dyad Y32 of MTX, and the H399T replacement made Kv1.3 sensitive to MTX, while the V381H mutation in hKv1.2 drastically reduced MTX binding affinity (Visan et al., 2004b).

The phenylalanine found in AnTx has a similar aromatic nature as tyrosine, so this toxin's poor selectivity for Kv1.3 is not surprising. The more polar side chains of threonine and asparagine appear to steer selectivity toward Kv1.3 over Kv1.2. Interestingly, the mutant [E16K, K20D]-OSK1 having T36 at the aromatic dyad position had somewhat lower Kv1.3 vs. Kv1.2 selectivity than its [E16K, K20D, T36Y]-OSK1 counterpart, implying that the outcome of the threonine/tyrosine exchange alone is not predictable. Nevertheless, despite the above data advising against the substitution for tyrosine, we decided to first synthesize the [F32T]-AnTx mutant with the aim of improving Kv1.3 vs. Kv1.2 selectivity.

Positions corresponding to K16 and N17 of AnTx are occupied by residues with positively charged side chains (arginine and lysine) or the polar glutamine in all highly Kv1.2-selective toxins listed in the table. Docking simulations confirmed the importance of these residues: R14 of CoTx (corresponding to K16) and R19 of Pi4 (corresponding to N17) form salt bridges with negatively charged side chains of Kv1.2 residues (M'Barek et al., 2003; Jouirou et al., 2004). The lysine and asparagine residues of AnTx fit this pattern suggesting the importance of these positions in binding to Kv1.2. The presence of an acidic residue at the position corresponding to AnTx K16 (E19 in NxTx, D19 in BmKTX and D20 in KTX) favors Kv1.3 selectivity. This was supported by the 5-fold improvement in Kv1.3 selectivity of OSK1 by the K20D mutation. Founded on these observations we chose to generate the K16D mutants.

We also decided to replace the bulky basic or polar residues by alanine at the position corresponding to AnTx N17 hoping that this mutation enhances selectivity for Kv1.3. For this purpose we chose to generate the N17A mutant.

Although there are no residues in the N-terminal segment of the toxin sequences that were clearly identified as interacting partners with channel residues, the possible role of this region to binding cannot be ruled out. The N-terminal residue of AnTx is a pyroglutamate, which position is occupied by an asparagine in most toxins effective on Kv1.3, preceded by 3 or 4 hydrophobic residues, a feature, which is missing in the highly Kv1.2-selective toxins. As a preferred approach we synthesized a mutant in which the N-terminal pyroglutamate was replaced by the AAAN sequence.

Comparison of the sequences suggests that a C-terminal half of the toxin (here defined as the region downstream of the end of the α-helix, starting with K18 in AnTx) carrying a higher net positive charge favors binding to Kv1.3 over Kv1.2. By this criterion AnTx should prefer Kv1.3, since it has six basic residues and a histidine in this region, compared to the net three positive charges typically found in Kv1.2-selective toxins. Similarly, a methionine rather than an isoleucine two positions downstream of the critical lysine in AnTx implies higher Kv1.3-selectivity. The corresponding residues 128 of Pi4 and the equivalent 126 of Pi1 were found to interact with a valine residue of Kv1.2 underlining the influence of this position in contributing to selectivity. Although the methionine at this position is favorable from a selectivity point of view, the oxidation-sensitive sulfur atom of this residue is a disadvantage considering its instability and potential future pharmaceutical production and application (Pennington et al., 2009). To overcome this problem we plan to test a M25T mutation with the intent of conserving affinity and selectivity, but removing the problematic methionine.

Further Planned Mutations:

Residue N21 in MTX corresponding to H21 in AnTx was found to form a salt bridge with D363 of Kv1.2 (Visan et al., 2004a) and this residue is highly conserved among the Kv1.2-selective Pi toxins as well, while other Kv1.3-selective toxins have an aromatic residue at that position. Therefore a H21Y mutation was suggested to improve selectivity for Kv1.3.

K27 in MTX and the equivalent K35 of AgTx2-MTX (=K30 in AnTx) were found to be influential residues in binding to Kv1.2 (Pimentel et al., 2008), and toxins favoring Kv1.2 have a basic residue or a polar asparagine at this position. While several of the Kv1.3-selective toxins also have a K or R residue here, the sequence comparison suggest that Kv1.3-selectivity may benefit from a K30G mutation.

Testing and screening of further mutant toxins can be carried out by any method known in the art or by a method disclosed herein, e.g. by binding experiment and calculation of Kd values, in silico by docking experiments or in animal models.

Results

As a first step we tried to reproduce the effects of the natural anuroctoxin with the wild-type (WT) toxin produced by solid-state chemical synthesis. Our attempt was successful since the synthetic toxin (sWT) blocked Kv1.2 with a $K_d$=5.3 nM and Kv1.3 with $K_d$=0.3 nM compared to the respective values of 6.1 nM and 0.73 nM for the natural toxin.

Based on the analysis described above we synthesized the following mutants with the intent of improving toxin selectivity for Kv1.3 versus Kv1.2 while preserving or possibly even increasing affinity of the wild-type toxin for Kv1.3: (F32T); (K16D, F32T); (N17A, F32T), (K16D, N17A, F32T); (K16D, N17A, F32Y) and (N-AAAN, K16D, N17A, F32T).

Replacement of the phenylalanine at the aromatic dyad position by threonine surprisingly reduced toxin affinity about 26-fold for Kv1.3 ($K_d$=7.5 nM) compared to the sWT toxin, but the reduction was much more pronounced for Kv1.2: at 100 nM concentration very small amount of block was detected, the estimated increase in $K_d$ was about 1000-fold. Since the F32T mutation was a step in the correct direction, most additional mutations were introduced on this background. The (K16D, F32T) mutants showed slightly improved affinity for both Kv1.2 and Kv1.3, but its properties were not significantly better than the single F32T mutant. In contrast, while the affinity of (N17A, F32T) improved 5-fold for Kv1.2 compared to F32T alone, the increase was 12-fold for Kv1.3, resulting in a toxin with an affinity for Kv1.3 equaling that of the natural toxin ($K_d$=0.63 nM), but with an unexpectedly high, i.e. 2400-fold selectivity over Kv1.2 compared to the 9-fold of the natural toxin.

While the mutations drastically reduced toxin affinity toward Kv1.2, they may have improved it for other channels that were not blocked by the natural toxin. To assess this possibility we tested the mutants on two other relevant channels: Kv1.1, the channel most closely related to the other two, and $K_{Ca}3.1$, the $Ca^{2+}$ activated $K^+$ channel, which plays an important role in the activation of naïve and central memory T cells. The toxins were ineffective on both channels at 100 nM concentration indicating their high selectivity for Kv1.3.

Based on the success of the double mutants, we synthesized the (K16D, N17A, F32T) triple mutant, However, the affinity of this mutant was greatly reduced (>100-fold) compared to the natural toxin, proving that individual advantageous changes are not additive in their effects.

Comparison of Kv channel blocking toxin sequences reveals that several toxins have at least three consecutive residues with hydrophobic side chains at their N-terminus followed by an asparagine, suggesting the importance of this region in binding. To test this possibility we generated the (N-AAAN, K16D, N17A, F32T) mutant, i.e. the N-terminus pyroglutamate was replaced by the AAAN sequence on the triple mutant background. The affinity of this mutant was even worse than the triple mutant ($K_d$=394 nM), making it practically ineffective on Kv1.3.

Finally, the threonine at the aromatic dyad position of the (K16D, N17A, F32T) triple mutant was changed to tyrosine, a residue likely to increase affinity for Kv1.3 at the expense of decreasing selectivity against Kv1.2. The results confirmed this expectation as the toxin blocked Kv1.3 with reasonable affinity ($K_d$=1.4 nM), but also blocked Kv1.2 ($K_d$=23.5 nM) yielding a selectivity ratio (SR=$K_{d[}$1.2]/$K_{d[}$1.3]=17) only slightly better than the natural toxin (SR=9).

Determination of the 3-Dimensional Structure of the Peptides by NMR

The three-dimensional structure of the synthetic AnTx and that of one mutant N17A, F32T has been determined recently using standard solution NMR techniques. The H1 resonances were assigned with standard homonuclear NMR techniques. Most of the distance constrains were obtained from NOESY spectra in H2O; additional constraints were from NOESY D2O spectra. Most NOE data were obtained from resolved signals and by automatic assignments using CYANA 2 with simulated annealing algorithm, using 578 and 549 NOE for the synthetic wild type and the N17A/F32T variant of the peptide, respectively. The overlap of the two peptides (PyMOL) indicates significant differences in the orientation of the lysine 23, which might contribute to the differences in the selectivity of the peptides for Kv1.2 and Kv1.3.

Docking Experiments

Having the 3D structures of the peptides determined using NMR techniques (see above) it is possible to determine the interacting residues between the ion channels and the toxins (wild-type synthetic AnTx or N17A/F32T variant of the peptide) using in silico docking procedures. The three dimensional structures of the peptides can be docked onto the models of Kv1.3 and Kv1.2 channels with RosettaDock program. Monomeric pore-forming segments of Kv1.3 were homology modeled previously in the laboratory based on the coordinates of rKv1.2 channel (3lut) with Swiss Model suite (see Gurrola et al, Biochemistry, 51:4049-4061, 2012 and the corresponding references therein). Tetrameric channels were built with the symmetry parameters of the template with PDBe PISA web server and further refined with Modeller 9v2 program. The docking experiments may highlight the importance of the difference in lysine 23 orientation in the selectivity for Kv1.3 vs Kv1.2 and may predict further site-specific modifications in the peptide to improve its pharmacological profile.

Testing of the Peptides in Animal Models

The obtained peptides can be tested in model animals. For example experimental autoimmune encephalomyelitis (AT-EAE), a disease resembling multiple sclerosis, can be induced in rats by myelin basic protein (MBP)-activated CD4 T lymphocytes and the peptides of the invention can be administered in vivo to the animals after the onset of disease intraperitoneally or subcutaneously, as described by Beeton C et al. [Proc Natl Acad Sci USA 2006; 103:17414-17419.]. One of the commonly accepted disease model caused by skin-homing TEM cells is the skin lesion in Delayed-Type Hypersensitivity reaction. (DTH) (Soler D, Humphreys T L, Spinola S M and Campbell J J: CCR4Versus CCR10 in Human Cutaneous TH Lymphocyte Trafficking. Blood 101: 1677-1682, 2003). The wild-type synthetic AnTX peptide already was shown to inhibit DTH in rats thereby highlighting its potential beneficial effects in the management of autoimmune diseases [Varga Z. et al. (2012)].

EXAMPLES

1.3. Cells 1.3.1 Lymphocyte Separation

Kv1.3 currents were measured in human peripheral T lymphocytes. Heparinized human peripheral venous blood was obtained from healthy volunteers. Mononuclear cells were separated by Ficoll-Hypaque density gradient centrifugation. Collected cells were washed twice with $Ca^{2+}$ and $Mg^{2+}$ free Hank's solution containing 25 mM HEPES buffer (pH 7.4). Cells were cultured in a 5% $CO_2$ incubator at 37° C. in 24 well culture plates in RPMI-1640 supplements with 10% FCS (Sigma-Aldrich, Hungary) 100 μg/ml penicillin, 100 μg/ml streptomycin and 2 mM L-glutamine at $0.5\times10^6$/ml density for 3-4 days. The culture medium also contained 2.5 or 5 μg/ml of phytohemagglutinin A (PHA-P, Sigma-Aldrich Kft, Hungary) to increase $K^+$ channel expression [Bagdany M, et al. *Mol Pharmacol* 2005; 67:1034-1044].

1.3.2 Heterologous Expression of Channels

Cos-7 cells were transiently transfected with the plasmid for hIKCa1 (subcloned into the pEGFP-C1 (Clontech) in frame with GFP, a gift of H. Wulff, UC Davis, CA, USA); or co-transfected with plasmids for green fluorescence protein (GFP) and for hKv1.2 (pcDNA3/Hygro vector containing the full coding sequence for Kv1.2, a gift from S. Grissmer, U. of Ulm).

Transfections were done at a GFP:channel DNA molar ratio of 1:5 using Lipofectamine 2000 reagent according to the manufacturer's protocol (Invitrogen, Carlsbad, Calif., USA), and cultured under standard conditions. Currents were recorded 1 day after transfection. GFP positive transfectants were identified in a Nikon TE2000U fluorescence microscope. More than 70% of the GFP positive cells expressed the co-transfected ion channels.

Cos-7 cells were maintained in standard cell culturing conditions [Papp F et al. *Toxicon* 2009; 54:379-389]. Human embryonic kidney cells transformed with SV40 large T antigen (tsA201) were grown in Dulbecco's minimum essential medium-high glucose supplemented with 10% FBS, 2 mM 1-glutamine, 100 U/ml penicillin-G, and 100 μg/ml streptomycin (Invitrogen) at 37° C. in a 9% $CO_2$ and 95% air-humidified atmosphere. Cells were passaged twice per week after a 7-min incubation in Versene containing 0.2 g/L EDTA (Invitrogen).

1.4. Electrophysiology

Whole-cell currents were measured in voltage-clamped cells using Axopatch 200A and Multiclamp 700B amplifiers connected to a personal computer using Axon Digidata 1200 and 1322A data acquisition hardware, respectively (Molecular Devices Inc., Sunnyvale, Calif.). Series resistance compensation up to 70% was used to minimize voltage errors and achieve good voltage-clamp conditions. Cells were observed with Nikon TE2000-U or Leitz Fluovert fluorescence microscopes using bandpass filters of 455-495 nm and 515-555 nm for excitation and emission, respectively. Cells displaying strong fluorescence were selected for current recording and >70 percent of these cells displayed co-transfected current. Pipettes were pulled from GC 150 F-15 borosilicate glass capillaries in five stages and fire-polished, resulting in electrodes having 3 to 5 MΩ resistance in the bath. For the measurement of most channels the bath solution consisted of (in mM) 145 NaCl, 5 KCl, 1 $MgCl_2$, 2.5 $CaCl_2$, 5.5 glucose, and 10 HEPES, pH 7.35, supplemented with 0.1 mg/ml bovine serum albumin (Sigma-Aldrich). The measured osmolarity of the external solutions was between 302 and 308 mOsm. The internal solution consisted of (in mM) 140 KF, 2 $MgCl_2$, 1 $CaCl_2$, 10 HEPES, and 11 EGTA, pH 7.22. For the recording of hIKCa1 currents the composition of the pipette filling solution was (in mM) 150 K-aspartate, 5 HEPES, 10 EGTA, 8.7 $CaCl_2$, 2 $MgCl_2$, (pH 7.2). This solution contained 1 μM free $Ca^{2+}$ concentration to fully activate the hIKCa1 current. The measured osmolarity of the internal solutions was approximately 295 mOsm. Bath perfusion around the measured cell with different test solutions was achieved using a gravity-flow perfusion system. Excess fluid was removed continuously. For data acquisition and analysis, the pClamp8/10 software package (Molecular Devices Inc., Sunnyvale, Calif.) was used. Generally, currents were low-pass filtered using the built in analog 4-pole Bessel filters of the amplifiers and sampled (2-50 kHz) at least twice the filter cut-off frequency. Before analysis, whole-cell current traces were corrected for ohmic leakage and digitally filtered (three-point boxcar smoothing). Each data point on the concentration-response curve represents the mean of 3-7 independent experiments, and error bars represent SEM. Data points were fitted with a two parameter Hill-equation: $RCF=K_d^n/(K_d^n+[Tx]^n)$, where RCF is the Remaining Current Fraction ($RCF=I/I_0$, where I and $I_0$ are the current amplitudes in the presence and absence of the toxin of given concentration, respectively), $K_d$ is the dissociation constant, n is the Hill coefficient and [Tx] is the toxin concentration.

Solid Phase Synthesis of Toxins

1. AnTx (SEQ ID NO: 1)

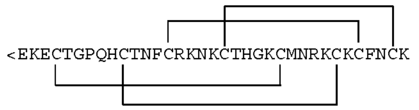

For the synthesis of the linear sequence of the peptide toxin AnTx (Anuroctoxin):

(<EKECTGPQHCTNFCRKNKCTHGKCMNRKCKCFNCK)

0.833 g (0.5 mmol) Boc-Lys(2ClZ)-PAM resin (loading: 0.6 mmol/g) was pre-swollen in dichloromethane and treated twice with 10% (v/v) TEA/DCM (2×1 min; 10-10 ml) and then washed successively with 10-10 ml DCM (3×), MeOH (1×) and DCM (3×). For Boc-deprotection the peptide resin was treated twice with 50% (v/v) TFA in DCM (1×5 min, 1×25 min; 10-10 nil), then washed with 10-10 ml DCM (2×), MeOH (2×) and DCM (2×), followed by neutralization with 10% (v/v) TEA in DCM (2×1 min; 10 ml) and another washing steps (with 10-10 nil solvent): DCM (3×), MeOH (1×), DCM (3×). Chain elongation with Boc-amino acids was performed by couplings with three equivalents of Boc-amino acid (1.5 mmol), N,N'-Dicyclohexyl-carbodiimide (0.309 g, 1.5 mmol) and N-Hydroxybenzotriazole (0.202 g, 1.5 mmol) in 10 ml DCM for 3 hours, followed by washings with 10-10 ml DCM (3×), MeOH (2×) and DCM (3×). The coupling efficiency was monitored with the Kaiser test. Amino acids used for further chain elongation: Boc-L-Asn-OH ($M_w$=232.2; 0.348 g, 1.5 mmol), Boc-L-Arg(Tos)-OH ($M_w$=516.6; 0.775 g), Boc-L-Cys(Meb)-OH ($M_w$=325.43; 0.488 g; 1.5 mmol), Boc-L-Gly-OH ($M_w$=175.2; 0.262 g, 1.5 mmol), Boc-L-Gln-OH ($M_w$=246.5; 0.369 g, 1.5 mmol), Boc-L-Glu(OcHx)-OH ($M_w$=329.39; 0.494 g, 1.5 mmol), Boc-L-Lys(2ClZ)-OH ($M_w$=414.9; 0.622 g, 1.5 mmol), Boc-L-His(Z)-OH ($M_w$=389.41; 0.584 g, 1.5 mmol), Boc-L-Met-OH ($M_w$=249.3; 0.374 g, 1.5 mmol), Boc-L-Phe-OH ($M_w$=265.13; 0.397 g, 1.5 mmol), Boc-L-Pro-OH ($M_w$=215.25; 0.322 g, 1.5 mmol), Boc-L-Thr(Bzl)-OH ($M_w$=309.4; 0.464 g, 1.5 mmol), H-L-pGlu-OH ($M_w$=129.12; 0.193 g, 1.5 mmol). Cleavage of the peptide from the resin was performed by addition of a mixture containing 20 ml HF, 0.4 ml anisol, 1.6 ml dimethyl-sulfide, 0.4 mlp-cresol and 0.3 g DTT for 45 minutes at −5° C. After cleavage, the peptide was precipitated onto the resin in ice cold diethyl ether and lyophilized after solubilization in 10 ml 10% (v/v) acetic acid and 100 ml $H_2O$. The crude peptide was analysed by RP-HPLC using (A) 0.1% TFA and (B) 80% MeCN, 0.1% TFA as eluents. Elution was conducted at a flow rate of 1.2 ml/min and detection was performed at 220 nm. Mass of the crude linear peptide: 1.690 g; $t_R$=12.43 (column: Phenomenex Jupiter 5 μm C18 300 Å, 250×4.60 mm; the linear gradient used: 10-30% (B); 20 min). The peptide was characterized by measurement of its mass by mass spectrometry: $M_{calcd}$=4108.8; $M_{found}$=4109 ($[M+H]^+$; MS: ($ESI^+$): m/z).

Cyclization was performed with 20 μmol of the linear peptid: 0.082 g peptide was dissolved in 164 ml Gly-NaOH buffer (pH 8.7) and left to stir 24 hours. After lyophilization, the oxidized peptide was purified by RP-HPLC and characterized by analytical RP-HPLC and mass spectrometry: $t_R$=9.22 (column: Phenomenex Jupiter 5 μm C18 300 Å, 250×4.60 mm; the linear gradient used: 10-30% (B); 20 min); $M_{calcd}$=4100.8; $M_{found}$=4101 ($[M+H]^+$; MS: ($ESI^+$): m/z).

2. AnTx F32T (SEQ ID NO: 2)

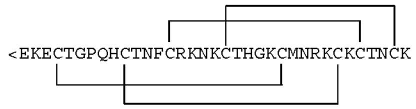

For the synthesis of the linear sequence of the peptide toxin AnTx F32T:

(<EKECTGPQHCTNFCRKNKCTHGKCMNRKCKCTNCK)

1.25 g (0.25 mmol) TentaGel R PHB resin (loading: 0.2 mmol/g) was used, the synthesis was performed with a CEM microwave peptide synthesizer. For Fmoc-deprotection 20% (v/v) piperidine in DMF was applied, coupling of Fmoc-protected amino acids (1 mmol) was performed with 4-4 equivalents of HBTU and HOBt, as activator base DIEA was applied. Amino acids used for chain elongation were: Fmoc-L-Asn(Trt)-OH ($M_w$=596.7; 0.596 g, 1 mmol), Fmoc-L-Arg(Pbf)-OH ($M_w$=648.8; 0.648 g, 1 mmol), Fmoc-L-Cys(Trt)-OH ($M_w$=585.7; 0.585 g, 1 mmol), Fmoc-L-Gly-OH ($M_w$=297.3; 0.297 g, 1 mmol), Fmoc-L-Gln(Trt)-OH ($M_w$=610.7; 0.610 g, 1 mmol), Fmoc-L-Glu(OtBu)-OH.$H_2O$ ($M_w$=443.5; 0.443 g, 1 mmol), Fmoc-L-Lys(Boc)-OH ($M_w$=468.5; 0.468 g, 1 mmol), Fmoc-L-His-OH ($M_w$=619; 0.619 g, 1 mmol), Fmoc-L-Met-OH ($M_w$=371.5; 0.371 g, 1 mmol), Fmoc-L-Phe-OH ($M_w$=387; 0.387 g, 1 mmol), Fmoc-L-Pro-OH ($M_w$=337.4; 0.337 g, 1 mmol), Fmoc-L-Thr(tBu)-OH ($M_w$=397.2; 0.397 g, 1 mmol), H-L-pGlu-OH ($M_w$=129.12; 0.129 g, 1 mmol). Cleavage of the peptide from the resin was performed by addition of a mixture of 12.45 ml TFA, 1.5 ml $H_2O$, 750 mg DTT, 0.3 ml TIS for 3 hours at room temperature. After cleavage, the peptide was precipitated onto the resin in ice cold diethyl ether and lyophilized after solubilization in 10 ml 10% (v/v) acetic acid and 100 ml $H_2O$. The crude peptide was analysed by RP-HPLC using (A) 0.1% TFA and (B) 80% MeCN, 0.1% TFA as eluents. Elution was conducted at a flow rate of 1.0 ml/min and detection was performed at 220 nm. Mass of the crude linear peptide: 0.675 g;

The CEM method applied was the following:

| CEM Method | Cycle | Nr. of cycles | Microwave power (W) | Max. Temperature (° C.) | Reaction time (sec) |
|---|---|---|---|---|---|
| Fmoc- | simple | 1 | 35 | 75 | 30 |
| deprotection | | 1 | 40 | 75 | 180 |
| Coupling | simple | 1 | 26 | 75 | 300 |
| Cys, Hys | double | 2 | 0 | 50 | 120 |
| coupling | | | 25 | 50 | 240 |
| Arg coupling | double | 2 | 0 | 75 | 1500 |
| | | | 25 | 75 | 30 |

Cyclization was performed with 20 μmol of the linear peptid: 0.080 g peptide was dissolved in 160 ml Gly-NaOH buffer (pH 8.7) and left to stir 24 hours. After lyophilization, the oxidized peptide was purified by RP-HPLC and characterized by analytical RP-HPLC and mass spectrometry: $t_R$=8.585 (column: Phenomenex Luna 5 μm C18(2) 100 Å, 250×4.60 mm; the linear gradient used: 10-25% (B); 15 min); $M_{calcd}$=4036.7; $M_{found}$=4037 ([M+H]$^+$; MS: (ESI$^+$): m/z).

3. AnTx F32T, K16D (SEQ ID NO: 3)

<EKECTGPQHCTNFCRDNKCTHGKCMNRKCKCTNCK

The synthetic peptide toxin AnTx F32T, N17A was prepared with the same procedure as described in example 2. Amino acids used for chain elongation were: Fmoc-L-Asn (Trt)-OH ($M_w$=596.7; 0.596 g, 1 mmol), Fmoc-L-Asp (OtBu)-OH ($M_w$=411.5; 0.411 g, 1 mmol), Fmoc-L-Arg (Pbf)-OH ($M_w$=648.8; 0.648 g, 1 mmol), Fmoc-L-Cys(Trt)-OH ($M_w$=585.7; 0.585 g, 1 mmol), Fmoc-L-Gly-OH ($M_w$=297.3; 0.297 g, 1 mmol), Fmoc-L-Gln(Trt)-OH ($M_w$=610.7; 0.610 g, 1 mmol), Fmoc-L-Glu(OtBu)-OH.$H_2O$ ($M_w$=443.5; 0.443 g, 1 mmol), Fmoc-L-Lys(Boc)-OH ($M_w$=468.5; 0.468 g, 1 mmol), Fmoc-L-His-OH ($M_w$=619; 0.619 g, 1 mmol), Fmoc-L-Met-OH ($M_w$=371.5; 0.371 g, 1 mmol), Fmoc-L-Phe-OH ($M_w$=387; 0.387 g, 1 mmol), Fmoc-L-Pro-OH ($M_w$=337.4; 0.337 g, 1 mmol), Fmoc-L-Thr(tBu)-OH ($M_w$=397.2; 0.397 g, 1 mmol), H-L-pGlu-OH ($M_w$=129.12; 0.129 g, 1 mmol). Mass of the crude linear peptide: 0.670 g.

Analytical characterization of the cyclic peptide was performed by analytical RP-HPLC and mass spectometry: $t_R$=8.46 (column: Phenomenex Luna 5 μm C18(2) 100 Å, 250×4.60 mm; the linear gradient used: 10-25% (B); 15 min); $M_{calcd}$=4024.6; $M_{found}$=4025 ([M+H]$^+$; MS: (ESI$^+$): m/z).

4. AnTx F32T, N17A (SEQ ID NO: 4)

<EKECTGPQHCTNFCRKAKCTHGKCMNRKCKCTNCK

The synthetic peptide toxin AnTx F32T, N17A was prepared with the same procedure as described in example 2. Amino acids used for chain elongation were: Fmoc-L-Ala-OH.$H_2O$ ($M_w$=329.36; 0.329 g, 1 mmol), Fmoc-L-Asn(Trt)-OH ($M_w$=596.7; 0.596 g, 1 mmol), Fmoc-L-Arg(Pbf)-OH ($M_w$=648.8; 0.648 g, 1 mmol), Fmoc-L-Cys(Trt)-OH ($M_w$=585.7; 0.585 g, 1 mmol), Fmoc-L-Gly-OH ($M_w$=297.3; 0.297 g, 1 mmol), Fmoc-L-Gln(Trt)-OH ($M_w$=610.7; 0.610 g, 1 mmol), Fmoc-L-Glu(OtBu)-OH.$H_2O$ ($M_w$=443.5; 0.443 g, 1 mmol), Fmoc-L-Lys(Boc)-OH ($M_w$=468.5; 0.468 g, 1 mmol), Fmoc-L-His-OH ($M_w$=619; 0.619 g, 1 mmol), Fmoc-L-Met-OH ($M_w$=371.5; 0.371 g, 1 mmol), Fmoc-L-Phe-OH ($M_w$=387; 0.387 g, 1 mmol), Fmoc-L-Pro-OH ($M_w$=337.4; 0.337 g, 1 mmol), Fmoc-L-Thr(tBu)-OH ($M_w$=397.2; 0.397 g, 1 mmol), H-L-pGlu-OH ($M_w$=129.12; 0.129 g, 1 mmol). Mass of the crude linear peptide: 0.623 g.

Analytical characterization of the cyclic peptide was performed by analytical RP-HPLC and mass spectometry: $t_R$=10.09 (column: Phenomenex Luna 5 μm C18(2) 100 Å, 250×4.60 mm; the linear gradient used: 10-25% (B); 15 min); $M_{calcd}$=3999.7; $M_{found}$=4000 ([M+H]$^+$; MS: (ESI$^+$): m/z).

5. AnTx F32T, K16D, N17A (SEQ ID NO: 5)

<EKECTGPQHCTNFCRDAKCTHGKCMNRKCKCTNCK

The synthetic peptide toxin AnTx F32T, NI 7A was prepared with the same procedure as described in example 2. Amino acids used for chain elongation were: Fmoc-L-Ala-OH.$H_2O$ ($M_w$=329.36; 0.329 g, 1 mmol), Fmoc-L-Asn(Trt)-OH ($M_w$=596.7; 0.596 g, 1 mmol), Fmoc-L-Asp(OtBu)-OH ($M_w$=411.5; 0.411 g, 1 mmol), Fmoc-L-Arg(Pbf)-OH ($M_w$=648.8; 0.648 g, 1 mmol), Fmoc-L-Cys(Trt)-OH ($M_w$=585.7; 0.585 g, 1 mmol), Fmoc-L-Gly-OH ($M_w$=297.3; 0.297 g, 1 mmol), Fmoc-L-Gln(Trt)-OH ($M_w$=610.7; 0.610 g, 1 mmol), Fmoc-L-Glu(OtBu)-OH.$H_2O$ ($M_w$=443.5; 0.443 g, 1 mmol), Fmoc-L-Lys(Boc)-OH ($M_w$=468.5; 0.468 g, 1 mmol), Fmoc-L-His-OH ($M_w$=619; 0.619 g, 1 mmol), Fmoc-L-Met-OH ($M_w$=371.5; 0.371 g, 1 mmol), Fmoc-L-Phe-OH ($M_w$=387; 0.387 g, 1 mmol), Fmoc-L-Pro-OH ($M_w$=337.4; 0.337 g, 1 mmol), Fmoc-L-Thr(tBu)-OH ($M_w$=397.2; 0.397 g, 1 mmol), H-L-pGlu-OH ($M_w$=129.12; 0.129 g, 1 mmol). Mass of the crude peptide: 0.630 g.

Analytical characterization of the cyclic peptide was performed by analytical RP-HPLC and mass spectometry: $t_R$=11.73 (column: Phenomenex Luna 5 μm C18(2) 100 Å, 250×4.60 mm; the linear gradient used: 10-30% (B); 20 min); $M_{calcd}$=3981.5; $M_{found}$=3982 ([M+H]$^+$; MS: (ESI$^+$): m/z).

6. AnTx F32T, K16D, N17A, pGlu1AAAN (SEQ ID NO: 6)

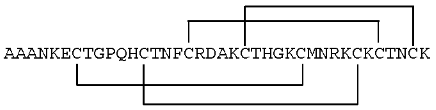

The synthetic peptide toxin AnTx F32T, N17A was prepared with the same procedure as described in example 2. Amino acids used for chain elongation were: Fmoc-L-Ala-OH.$H_2O$ ($M_w$=329.36; 0.329 g, 1 mmol), Fmoc-L-Asn(Trt)-OH ($M_w$=596.7; 0.596 g, 1 mmol), Fmoc-L-Asp(OtBu)-OH ($M_w$=411.5; 0.411 g, 1 mmol), Fmoc-L-Arg(Pbf)-OH ($M_w$=648.8; 0.648 g, 1 mmol), Fmoc-L-Cys(Trt)-OH ($M_w$=585.7; 0.585 g, 1 mmol), Fmoc-L-Gly-OH ($M_w$=297.3; 0.297 g, 1 mmol), Fmoc-L-Gln(Trt)-OH ($M_w$=610.7; 0.610 g, 1 mmol), Fmoc-L-Glu(OtBu)-OH.$H_2O$ ($M_w$=443.5; 0.443 g, 1 mmol), Fmoc-L-Lys(Boc)-OH ($M_w$=468.5; 0.468 g, 1 mmol), Fmoc-L-His-OH ($M_w$=619; 0.619 g, 1 mmol), Fmoc-L-Met-OH ($M_w$=371.5; 0.371 g, 1 mmol), Fmoc-L-Phe-OH ($M_w$=387; 0.387 g, 1 mmol), Fmoc-L-Pro-OH ($M_w$=337.4; 0.337 g, 1 mmol), Fmoc-L-Thr(tBu)-OH ($M_w$=397.2; 0.397 g, 1 mmol), H-L-pGlu-OH ($M_w$=129.12; 0.129 g, 1 mmol). Mass of the crude peptide: 0.680 g.

Analytical characterization of the cyclic peptide was performed by analytical RP-HPLC and mass spectometry: $t_R$=8.08 (column: Phenomenex Luna 5 μm C18(2) 100 Å, 250×4.60 mm; the linear gradient used: 10-30% (B); 20 min); $M_{calcd}$=4197.8; $M_{found}$=4198 ($[M+H]^+$; MS: ($ESI^+$): m/z).

REFERENCES

Bagdany M, Batista C V, Valdez-Cruz N A et al. Anuroctoxin, a new scorpion toxin of the alpha-KTx 6 subfamily, is highly selective for Kv1.3 over IKCa1 ion channels of human T lymphocytes. Mol Pharmacol 2005; 67:1034-1044.

Batista C V, Gomez-Lagunas F, Rodríguez de la Vega R C et al. Two novel toxins from the Amazonian scorpion Tityus cambridgei that block Kv1.3 and Shaker B K(+)-channels with distinctly different affinities. Biochim Biophys Acta 2002; 1601:123-131.

Beeton C, Wulff H, Barbaria J et al. Selective blockade of T lymphocyte K+ channels ameliorates experimental autoimmune encephalomyelitis, a model for multiple sclerosis. Proc Natl Acad Sci USA 2001; 98:13942-13947.

Beeton C, Wulff H, Standifer N E et al. Kv1.3 channels are a therapeutic target for T cell-mediated autoimmune diseases. Proc Natl Acad Sci USA 2006; 103:17414-17419.

Corzo G, Papp F, Varga Z et al. A selective blocker of Kv1.2 and Kv1.3 potassium channels from the venom of the scorpion Centruroides suffusus suffusus. Biochem Pharmacol 2008; 76:1142-1154.

Dauplais M, Lecoq A, Song J et al. On the convergent evolution of animal toxins. Conservation of a diad of functional residues in potassium channel-blocking toxins with unrelated structures. J Biol Chem 1997; 272:4302-4309.

Desir G, Xu J, Koni P A, Kaczmarek L, Flavell R A, Compositions and methods relating to glucose metabolism, weight control and food intake U.S. Pat. No. 6,861,405 (2005)

Goldstein S A, Miller C. Mechanism of charybdotoxin block of a voltage-gated K+ channel. Biophys J 1993; 65:1613-1619.

Han S, Yi H, Yin S J, Chen Z Y, Liu H, Cao Z J, Wu Y L, and Li W X Structural Basis of a Potent Peptide Inhibitor Designed for Kv1.3 Channel, a Therapeutic Target of Autoimmune Disease J Biol Chem 2008; 283(27):19058-19065.

Jouirou B, Mosbah A, Visan V et al. Cobatoxin 1 from Centruroides noxius scorpion venom: chemical synthesis, three-dimensional structure in solution, pharmacology and docking on K+ channels. Biochem J 2004; 377:37-49.

Leonard R J, Garcia M L, Slaughter R S, Reuben J P. Selective blockers of voltage-gated K+ channels depolarize human T lymphocytes: mechanism of the antiproliferative effect of charybdotoxin. Proc Natl Acad Sci USA 1992; 89:10094-10098.

M'Barek S, Mosbah A, Sandoz G et al. Synthesis and characterization of Pi4, a scorpion toxin from Pandinus imperator that acts on K+ channels. Eur J Biochem 2003; 270: 3583-3592.

Mouhat S, Mosbah A, Visan V et al. The 'functional' dyad of scorpion toxin Pi1 is not itself a prerequisite for toxin binding to the voltage-gated Kv1.2 potassium channels. Biochem J 2004; 377:25-36.

Mouhat S, Sabatier J M, De Rougé B O, OsK1 Derivatives WO2006002850A2 2006

Panyi G, Possani L D, Rodriguez de la Vega R C, Gaspar R, Varga Z. K+ channel blockers: novel tools to inhibit T cell activation leading to specific immunosuppression. Curr Pharm Des 2006; 12:2199-2220.

Panyi G, Varga Z, Gaspar R. Ion channels and lymphocyte activation. Immunol Lett 2004; 92:55-66.

Papp F, Batista C V, Varga Z et al. Tst26, a novel peptide blocker of Kv1.2 and Kv1.3 channels from the venom of *Tityus stigmurus*. Toxicon 2009; 54:379-389.

Pennington M W, Beeton C, Galea C A et al. Engineering a stable and selective peptide blocker of the Kv1.3 channel in T lymphocytes. Mol Pharmacol 2009; 75:762-773.

Peter M, Hajdu P, Varga Z et al. Blockage of human T lymphocyte Kv1.3 channels by Pi1, a novel class of scorpion toxin. Biochem Biophys Res Commun 2000; 278:34-37.

Peter M J, Varga Z, Hajdu P et al. Effects of toxins Pi2 and Pi3 on human T lymphocyte Kv1.3 channels: the role of Glu7 and Lys24. J Membr Biol 2001; 179:13-25.

Pimentel C, M'Barek S, Visan V et al. Chemical synthesis and $^1$H-NMR 3D structure determination of AgTx2-MTX chimera, a new potential blocker for Kv1.2 channel, derived from MTX and AgTx2 scorpion toxins. Protein Sci 2008; 17:107-118.

Srinivasan K N, Sivaraja V, Huys I et al. kappa-Hefutoxin1, a novel toxin from the scorpion (Srinivasan et al., 2002) heterometrus fulvipes with unique structure and function: Importance of the functional diad in potassium channel selectivity. J Biol Chem 2002; 277:30040-30047.

Sullivan J K, McGivern J G, Miranda L P, Nguyen H Q, Walker K W, HU SFS, Gegg C V, McDonough S I, Toxin peptide therapeutic agents US2007/0071764 2007

Tucker K, Overton J M and Fadool D A, Kv1.3 gene-targeted deletion alters longevity and reduces adiposity by increasing locomotion and metabolism in melanocortin-4 receptor-null mice International Journal of Obesity (2008), 1-11

Visan V, Fajloun Z, Sabatier J M, Grissmer S. Mapping of maurotoxin binding sites on hKv1.2, hKv1.3, and hIKCa1 channels. Mol Pharmacol 2004; 66:1103-1112.

Varga Z, Gurrola-Briones G, Papp F, Rodríguez de la Vega R C, Pedraza-Alva G, Tajhya R B, Gaspar R, Cardenas L, Rosenstein Y, Becton C, Possani L D, Panyi G. Vm24, a natural immunosuppressive peptide, potently and selectively blocks Kv1.3 potassium channels of human T cells. Mol. Pharmacol. 2012 82(3):372-82.

Wulff H, Calabresi P A, Allie R et al. The voltage-gated Kv1.3 K+ channel in effector memory T cells as new target for MS. J Clin Invest 2003; 111:1703-1713.

Yin S J, Jiang L, Yi H, Han S, Yang D W, Liu M L, Liu H, Cao Z J, Wu Y L, and Li W X Different Residues in Channel Turret Determining the Selectivity of ADWX-1 Inhibitor Peptide between Kv1.1 and Kv1.3 Channels J Prot Res 2008; 7(11):4890-4897

The invention claimed is:

1. A toxin peptide capable of selectively inhibiting a Kv1.3 potassium channel protein, said peptide having 32 to 36 amino acid residues, said peptide having four disulphide bridges, wherein said peptide comprises the following amino acid sequence:

(SEQ ID NO: 7)

| | | | | | | | | | |
|---|---|---|---|---|---|---|---|---|---|
| 1 | 2 | 3 | 4 | 5 | 6 | 7 | 8 | 9 | 10 |
| Z | $X_1$ | $X_2$ | $C_1$ | $X_3$ | $X_4$ | $X_5$ | $X_6$ | $X_7$ | $C_2$ |
| 11 | 12 | 13 | 14 | 15 | 16 | 17 | 18 | 19 | 20 |
| $X_8$ | $X_9$ | $X_{10}$ | $C_3$ | $X_{11}$ | $X_{12}$ | $X_{13}$ | $K_1$ | $C_4$ | $T_1$ |
| 21 | 22 | 23 | 24 | 25 | 26 | 27 | 28 | 29 | 30 |
| $X_{14}$ | $G_1$ | $K_2$ | $C_5$ | $X_{15}$ | $N_1$ | $R_1$ | $K_3$ | $C_6$ | $X_{16}$ |
| 31 | 32 | 33 | 34 | 35 | | | | | |
| $C_7$ | $T_1$ | $N_2$ | $C_8$ | $X_{17}$ | | | | | |

wherein

| Pos. | |
|---|---|
| 1 | Z is pyroglutamate, glutamate (E), aspartate (D), asparagine (N) or glutamine (Q), |
| 2 | $X_1$ is lysine (K) or arginine (R) or nothing, |
| 3 | $X_2$ is glutamate (E) or aspartate (D) or nothing, |
| 4 | $C_1$ is cysteine (C), |
| 5 | $X_3$ is threonine (T) or serine (S), |
| 6 | $X_4$ is glycine (G) or alanine (A), |
| 7 | $X_5$ is proline (P) or serine (S), |
| 8 | $X_6$ is glutamine (Q), asparagine (N), glutamate (E), aspartate (D) or lysine (K), |
| 9 | $X_7$ histidine (H), phenylalanine (F), aspartate (D) or glutamine (Q), |
| 10 | $C_2$ is cysteine (C), |
| 11 | $X_8$ is threonine (T), serine (S), alanine (A), leucine (L) or isoleucine (I), |
| 12 | $X_9$ is asparagine (N), glutamate (E), glutamine (Q) or lysine (K), |
| 13 | $X_{10}$ is phenylalanine (F), proline (P) or histidine (H), |
| 14 | $C_3$ is cysteine (C), |
| 15 | $X_{11}$ is lysine (K) or arginine (R), |
| 16 | $X_{12}$ is lysine (K) or aspartate (D), |
| 17 | $X_{13}$ is alanine (A) or asparagine (N), |
| 18 | $K_1$ is lysine (K), |
| 19 | $C_4$ is cysteine (C), |
| 20 | $T_1$ is threonine (T), |
| 21 | $X_{14}$ is histidine (H) or tyrosine (Y), |
| 22 | $G_1$ is glycine (G), |
| 23 | $K_2$ is lysine (K), |
| 24 | $C_5$ is cysteine (C), |
| 25 | $X_{15}$ is methionine (M), threonine (T) or norleucine (Nor), |
| 26 | $N_1$ is asparagine (N), |
| 27 | $R_1$ is arginine (R) |
| 28 | $K_3$ is lysine (K), |
| 29 | $C_6$ is cysteine (C), |
| 30 | $X_{16}$ is lysine (K) or glycine (G) |
| 31 | $C_7$ is cysteine (C), |
| 32 | $T_1$ is threonine, |
| 33 | $N_2$ is asparagine (N), |
| 34 | $C_8$ is cysteine (C), and |
| 35 | $X_{17}$ is lysine (K) or arginine (R). |

2. The toxin peptide according to claim 1, wherein the toxin peptide is selected from the following group of peptides:

```
                                          (SEQ ID NO: 2)
<EKECTGPQHC TNFCRKNKCT HGKCMNRKCK CTNCK,
                                          (SEQ ID NO: 3)
<EKECTGPQHC TNFCRDNKCT HGKCMNRKCK CTNCK,
                                          (SEQ ID NO: 4)
<EKECTGPQHC TNFCRKAKCT HGKCMNRKCK CTNCK,
                                          (SEQ ID NO: 5)
<EKECTGPQHC TNFCRDAKCT HGKCMNRKCK CTNCK,
```

or a mutant or variant thereof comprising at most 12 amino acid substitutions as defined in claim 1 in the region spanning amino acids 1 to 15 of the toxin peptide sequence wherein the cysteine residues are maintained.

3. The toxin peptide according to claim 1, wherein the dissociation constant (Kd,Kv1.2) of the peptide for Kv1.2 potassium channel protein is higher than 1000 nM, the dissociation constant (Kd,Kv1.3) of the peptide for Kv1.3 potassium channel protein is lower than 10 nM, and/or wherein the selectivity of the toxin peptide for Kv1.3 against Kv1.2 (i.e. the ratio of Kd,Kv1.2 and Kd,Kv1.3) is higher than 100.

4. A method for treating a disease, selected from the group consisting of a T cell mediated autoimmune disorder, multiple sclerosis, systemic sclerosis, type-1 diabetes, rheumatoid arthritis, psoriatic arthritis, psoriasis, metabolic syndrome, obesity and type II diabetes mellitus, comprising the step of administering a toxin peptide according to claim 1 to a patient in need thereof in an amount effective to alleviate at least one symptom of said disease.

5. The toxin peptide of claim 1, wherein the Kv1.3 potassium channel protein is of vertebrate, mammalian or human origin.

6. The method of claim 4, wherein the Kv1.3 potassium channel protein is of vertebrate, mammalian or human origin.

7. The toxin peptide of claim 1, wherein said peptide has 33, 34 or 35 amino acid residues.

8. The toxin peptide of claim 1, wherein if $X_{12}$ is lysine (K) then $X_{13}$ is alanine (A) or asparagine (N), and whereas if $X_{12}$ is aspartate (D) then $X_{13}$ is asparagine (N).

9. The toxin peptide of claim 2, wherein the mutant or variant thereof comprises at most 6 amino acid substitutions.

10. The toxin peptide of claim 3, wherein the dissociation constant (Kd,Kv1.2) of the peptide for Kv1.2 potassium channel protein is higher than 1200 nM.

11. The toxin peptide of claim 3, wherein the dissociation constant (Kd,Kv1.2) of the peptide for Kv1.2 potassium channel protein is higher than 1500 nM.

12. The toxin peptide of claim 3, wherein the dissociation constant (Kd,Kv1.3) of the peptide for Kv1.3 potassium channel protein is lower than 7 nM.

13. The toxin peptide of claim 3, wherein the dissociation constant (Kd,Kv1.3) of the peptide for Kv1.3 potassium channel protein is lower than 3 nM.

14. The toxin peptide of claim 3, wherein the dissociation constant (Kd,Kv1.3) of the peptide for Kv1.3 potassium channel protein is lower than 1 nM.

15. The toxin peptide of claim 3, wherein the selectivity of the toxin peptide for Kv1.3 against Kv1.2 is higher than 400.

16. The toxin peptide of claim 3, wherein the selectivity of the toxin peptide for Kv1.3 against Kv1.2 is higher than 700.

17. The toxin peptide of claim 3, wherein the selectivity of the toxin peptide for Kv1.3 against Kv1.2 is higher than 1000.

18. The toxin peptide of claim 3, wherein the selectivity of the toxin peptide for Kv1.3 against Kv1.2 is higher than 2000.

19. The toxin peptide of claim 3, wherein the selectivity of the toxin peptide for Kv1.3 against Kv1.2 is higher than 2100, 2200 or 2300.

20. The method of claim 4, wherein a T cell mediated autoimmune disorder is treated.

21. The method of claim 4, wherein multiple sclerosis, systemic sclerosis, type-1 diabetes, rheumatoid arthritis, psoriatic arthritis, or psoriasis is treated.

22. The method of claim 4, wherein obesity or type II diabetes mellitus is treated.

* * * * *

SEQUENCE LISTING

```
<160> NUMBER OF SEQ ID NOS: 7

<210> SEQ ID NO 1
<211> LENGTH: 35
<212> TYPE: PRT
<213> ORGANISM: Artificial Sequence
<220> FEATURE:
<223> OTHER INFORMATION: Anuroctonus phaiodactilus toxin (Anurotoxin)
<220> FEATURE:
<221> NAME/KEY: MISC_FEATURE
<222> LOCATION: (1)..(1)
<223> OTHER INFORMATION: Xaa is pyroglutamate

<400> SEQUENCE: 1

Xaa Lys Glu Cys Thr Gly Pro Gln His Cys Thr Asn Phe Cys Arg Lys
1               5                   10                  15

Asn Lys Cys Thr His Gly Lys Cys Met Asn Arg Lys Cys Lys Cys Phe
            20                  25                  30

Asn Cys Lys
        35


<210> SEQ ID NO 2
<211> LENGTH: 35
<212> TYPE: PRT
<213> ORGANISM: Artificial Sequence
<220> FEATURE:
<223> OTHER INFORMATION: Anuroctonus phaiodactilus toxin (Anurotoxin)
      F32T mutant
<220> FEATURE:
<221> NAME/KEY: MISC_FEATURE
<222> LOCATION: (1)..(1)
<223> OTHER INFORMATION: Xaa is pyroglutamate

<400> SEQUENCE: 2

Xaa Lys Glu Cys Thr Gly Pro Gln His Cys Thr Asn Phe Cys Arg Lys
1               5                   10                  15

Asn Lys Cys Thr His Gly Lys Cys Met Asn Arg Lys Cys Lys Cys Thr
            20                  25                  30

Asn Cys Lys
        35


<210> SEQ ID NO 3
<211> LENGTH: 35
<212> TYPE: PRT
<213> ORGANISM: Artificial Sequence
<220> FEATURE:
<223> OTHER INFORMATION: Anurotoxin F32T K16D mutant
<220> FEATURE:
<221> NAME/KEY: MISC_FEATURE
<222> LOCATION: (1)..(1)
<223> OTHER INFORMATION: Xaa is pyroglutamate

<400> SEQUENCE: 3

Xaa Lys Glu Cys Thr Gly Pro Gln His Cys Thr Asn Phe Cys Arg Asp
1               5                   10                  15

Asn Lys Cys Thr His Gly Lys Cys Met Asn Arg Lys Cys Lys Cys Thr
            20                  25                  30

Asn Cys Lys
        35
```

```
<210> SEQ ID NO 4
<211> LENGTH: 35
<212> TYPE: PRT
<213> ORGANISM: Artificial Sequence
<220> FEATURE:
<223> OTHER INFORMATION: Anurotoxin F32T N17A mutant
<220> FEATURE:
<221> NAME/KEY: MISC_FEATURE
<222> LOCATION: (1)..(1)
<223> OTHER INFORMATION: Xaa is pyroglutamate

<400> SEQUENCE: 4

Xaa Lys Glu Cys Thr Gly Pro Gln His Cys Thr Asn Phe Cys Arg Lys
1               5                   10                  15

Ala Lys Cys Thr His Gly Lys Cys Met Asn Arg Lys Cys Lys Cys Thr
            20                  25                  30

Asn Cys Lys
        35


<210> SEQ ID NO 5
<211> LENGTH: 35
<212> TYPE: PRT
<213> ORGANISM: Artificial Sequence
<220> FEATURE:
<223> OTHER INFORMATION: Anurotoxin F32T K16D N17A mutant
<220> FEATURE:
<221> NAME/KEY: MISC_FEATURE
<222> LOCATION: (1)..(1)
<223> OTHER INFORMATION: Xaa is pyroglutamate

<400> SEQUENCE: 5

Xaa Lys Glu Cys Thr Gly Pro Gln His Cys Thr Asn Phe Cys Arg Asp
1               5                   10                  15

Ala Lys Cys Thr His Gly Lys Cys Met Asn Arg Lys Cys Lys Cys Thr
            20                  25                  30

Asn Cys Lys
        35


<210> SEQ ID NO 6
<211> LENGTH: 38
<212> TYPE: PRT
<213> ORGANISM: Artificial Sequence
<220> FEATURE:
<223> OTHER INFORMATION: Anurotoxin AnTx F32T, K16D, N17A, pGlu1AAAN
      mutant

<400> SEQUENCE: 6

Ala Ala Ala Asn Lys Glu Cys Thr Gly Pro Gln His Cys Thr Asn Phe
1               5                   10                  15

Cys Arg Asp Ala Lys Cys Thr His Gly Lys Cys Met Asn Arg Lys Cys
            20                  25                  30

Lys Cys Thr Asn Cys Lys
        35


<210> SEQ ID NO 7
<211> LENGTH: 35
<212> TYPE: PRT
<213> ORGANISM: Artificial Sequence
<220> FEATURE:
<223> OTHER INFORMATION: General formula of mutant Anurotoxin peptides
<220> FEATURE:
<221> NAME/KEY: MISC_FEATURE
<222> LOCATION: (1)..(1)
<223> OTHER INFORMATION: Xaa can be pyroglutamate, glutamate (E),
      aspartate (D), asparagine (N) or glutamine (Q)
<220> FEATURE:
```

```
<221> NAME/KEY: MISC_FEATURE
<222> LOCATION: (2)..(2)
<223> OTHER INFORMATION: Xaa can be lysine (K) or arginine (R) or
      nothing
<220> FEATURE:
<221> NAME/KEY: MISC_FEATURE
<222> LOCATION: (3)..(3)
<223> OTHER INFORMATION: Xaa can be glutamate (E) or aspartate (D) or
      nothing
<220> FEATURE:
<221> NAME/KEY: MISC_FEATURE
<222> LOCATION: (5)..(5)
<223> OTHER INFORMATION: Xaa can be threonine (T) or serine (S)
<220> FEATURE:
<221> NAME/KEY: MISC_FEATURE
<222> LOCATION: (6)..(6)
<223> OTHER INFORMATION: Xaa can be glycine (G) or alanine (A)
<220> FEATURE:
<221> NAME/KEY: MISC_FEATURE
<222> LOCATION: (7)..(7)
<223> OTHER INFORMATION: Xaa can be proline (P) or serine (S)
<220> FEATURE:
<221> NAME/KEY: MISC_FEATURE
<222> LOCATION: (8)..(8)
<223> OTHER INFORMATION: Xaa can be glutamine (Q), asparagine (N),
      glutamate (E), aspartate (D) or lysine (K)
<220> FEATURE:
<221> NAME/KEY: MISC_FEATURE
<222> LOCATION: (9)..(9)
<223> OTHER INFORMATION: Xaa can be histidine (H), phenylalanine (F),
      aspartate (D) or glutamine (Q)
<220> FEATURE:
<221> NAME/KEY: MISC_FEATURE
<222> LOCATION: (11)..(11)
<223> OTHER INFORMATION: Xaa can be threonine (T), serine (S),
      alanine (A), leucine (L) or isoleucine (I)
<220> FEATURE:
<221> NAME/KEY: MISC_FEATURE
<222> LOCATION: (12)..(12)
<223> OTHER INFORMATION: Xaa can be asparagine (N), glutamate (E),
      glutamine (Q) or lysine (K)
<220> FEATURE:
<221> NAME/KEY: MISC_FEATURE
<222> LOCATION: (13)..(13)
<223> OTHER INFORMATION: Xaa can be phenylalanine (F), proline (P) or
      histidine (H)
<220> FEATURE:
<221> NAME/KEY: MISC_FEATURE
<222> LOCATION: (15)..(15)
<223> OTHER INFORMATION: Xaa can be lysine (K) or arginine (R)
<220> FEATURE:
<221> NAME/KEY: MISC_FEATURE
<222> LOCATION: (16)..(16)
<223> OTHER INFORMATION: Xaa can be lysine (K) or aspartate (D)
<220> FEATURE:
<221> NAME/KEY: MISC_FEATURE
<222> LOCATION: (17)..(17)
<223> OTHER INFORMATION: Xaa can be alanine (A) or asparagine (N)
<220> FEATURE:
<221> NAME/KEY: MISC_FEATURE
<222> LOCATION: (21)..(21)
<223> OTHER INFORMATION: Xaa can be histidine (H) or tyrosine (Y)
<220> FEATURE:
<221> NAME/KEY: MISC_FEATURE
<222> LOCATION: (25)..(25)
<223> OTHER INFORMATION: Xaa can be methionine (M), threonine (T) or
      norleucine (Nor)
<220> FEATURE:
<221> NAME/KEY: MISC_FEATURE
<222> LOCATION: (30)..(30)
<223> OTHER INFORMATION: Xaa can be lysine (K) or glycine (G)
<220> FEATURE:
<221> NAME/KEY: MISC_FEATURE
<222> LOCATION: (35)..(35)
<223> OTHER INFORMATION: Xaa can be lysine (K) or arginine (R)

<400> SEQUENCE: 7

Xaa Xaa Xaa Cys Xaa Xaa Xaa Xaa Xaa Cys Xaa Xaa Xaa Cys Xaa Xaa
```

-continued

```
1               5                   10                  15
Xaa Lys Cys Thr Xaa Gly Lys Cys Xaa Asn Arg Lys Cys Xaa Cys Thr
            20                  25                  30
Asn Cys Xaa
        35
```